United States Patent
Sherlock et al.

(10) Patent No.: US 11,325,941 B2
(45) Date of Patent: *May 10, 2022

(54) METHODS AND SYSTEMS FOR EXTRACTING REDUCED OXALIC ACID PROTEIN FROM AQUATIC SPECIES AND COMPOSITIONS THEREOF

(71) Applicant: Parabel Nutrition, Inc., Vero Beach, FL (US)

(72) Inventors: Peter Sherlock, Rockledge, FL (US); Matthew Neal Van Ert, Vero Beach, FL (US); Valentina Carpio, Fellsmere, FL (US)

(73) Assignee: Parabel Nutrition, Inc., Vero Beach, FL (US)

( * ) Notice: Subject to any disclaimer, the term of this patent is extended or adjusted under 35 U.S.C. 154(b) by 155 days.

This patent is subject to a terminal disclaimer.

(21) Appl. No.: 15/751,826

(22) PCT Filed: Aug. 10, 2016

(86) PCT No.: PCT/US2016/046422
§ 371 (c)(1),
(2) Date: Feb. 9, 2018

(87) PCT Pub. No.: WO2017/027634
PCT Pub. Date: Feb. 16, 2017

(65) Prior Publication Data
US 2018/0230179 A1    Aug. 16, 2018

Related U.S. Application Data

(60) Provisional application No. 62/203,199, filed on Aug. 10, 2015.

(51) Int. Cl.
C07K 1/14      (2006.01)
A23J 1/00      (2006.01)
(Continued)

(52) U.S. Cl.
CPC ............... *C07K 1/145* (2013.01); *A01H 4/00* (2013.01); *A01H 4/001* (2013.01); *A23J 1/006* (2013.01); *C07C 51/43* (2013.01)

(58) Field of Classification Search
CPC .............................. C07K 1/145; A23J 1/006
See application file for complete search history.

(56) References Cited

U.S. PATENT DOCUMENTS 2,522,513 A    9/1950 Hemmeter
2,692,200 A    10/1954 Olson
(Continued)

FOREIGN PATENT DOCUMENTS

CN    10111696     2/2008
CN    101116986    2/2008
(Continued)

OTHER PUBLICATIONS

"Nutritional Composition of Duckweed". Available online as of Dec. 31, 2011 from www.mobot.org. pp. 1-5. (Year: 2011).*
(Continued)

Primary Examiner — Jenna A Watts
(74) Attorney, Agent, or Firm — Baker & McKenzie LLP

(57) ABSTRACT

The present disclosure relates, according to some embodiments, to methods and systems for purifying proteins having a reduced oxalic acid content from aquatic species and compositions thereof.

36 Claims, 7 Drawing Sheets

(51) Int. Cl.
*A01H 4/00* (2006.01)
*C07C 51/43* (2006.01)

(56) References Cited

U.S. PATENT DOCUMENTS

| | | | |
|---|---|---|---|
| 2,827,454 A | 3/1958 | Nord | |
| 2,867,945 A | 1/1959 | Gotaas et al. | |
| 3,468,057 A | 9/1969 | Buisson et al. | |
| 3,499,687 A | 3/1970 | Ellis | |
| 3,674,501 A | 7/1972 | Betz et al. | |
| 3,704,041 A | 11/1972 | Loveland et al. | |
| 3,768,200 A | 10/1973 | Klock | |
| 3,839,198 A | 10/1974 | Shelef | |
| 3,930,450 A | 1/1976 | Symons | |
| 3,955,318 A | 5/1976 | Hulls | |
| 4,005,546 A | 2/1977 | Oswald | |
| 4,041,640 A | 8/1977 | Itanami et al. | |
| 4,042,367 A * | 8/1977 | Wilson | A01N 41/12 504/160 |
| 4,066,633 A | 1/1978 | Gastineau et al. | |
| 4,077,158 A | 3/1978 | England | |
| 4,137,868 A | 2/1979 | Pryor | |
| 4,253,271 A | 3/1981 | Raymond | |
| 4,429,867 A | 2/1984 | Barber | |
| 4,516,528 A | 3/1985 | Jones | |
| 4,557,937 A | 12/1985 | Bournier | |
| 4,560,032 A | 12/1985 | Imanaka | |
| 4,604,948 A | 8/1986 | Goldhahn | |
| 4,840,253 A | 6/1989 | DiMaggio et al. | |
| 4,910,912 A | 3/1990 | Lowrey, III | |
| 5,047,332 A | 9/1991 | Chahal | |
| 5,121,708 A | 6/1992 | Nuttle | |
| 5,171,592 A | 12/1992 | Holtzapple et al. | |
| 5,269,819 A | 12/1993 | Porath | |
| 5,527,456 A | 6/1996 | Jensen | |
| 5,659,977 A | 8/1997 | Jensen et al. | |
| 5,667,445 A | 9/1997 | Lochtefeld | |
| 5,704,733 A | 1/1998 | de Greef | |
| 5,941,165 A | 8/1999 | Butte | |
| 6,077,548 A | 6/2000 | Lasseur et al. | |
| 6,096,546 A | 8/2000 | Raskin | |
| 6,251,643 B1 | 6/2001 | Hansen et al. | |
| 6,348,347 B1 | 2/2002 | Hirabayashi et al. | |
| 7,058,197 B1 | 6/2006 | McGuire et al. | |
| 7,215,420 B2 | 5/2007 | Gellerman et al. | |
| 7,674,077 B2 | 3/2010 | Opatril | |
| 8,245,440 B2 | 8/2012 | Ryan et al. | |
| 8,287,740 B2 | 10/2012 | Newman et al. | |
| 8,722,878 B2 | 5/2014 | Raines et al. | |
| 9,675,054 B2 | 6/2017 | Grajcar et al. | |
| 2004/0030516 A1 | 2/2004 | Dunhill et al. | |
| 2004/0144025 A1 | 7/2004 | Rutzke | |
| 2006/0024689 A1 | 2/2006 | Bleuart et al. | |
| 2007/0048859 A1 | 3/2007 | Sears | |
| 2007/0151522 A1 | 7/2007 | Brauman | |
| 2008/0032349 A1 | 2/2008 | Visckov et al. | |
| 2008/0096267 A1 | 4/2008 | Howard et al. | |
| 2008/0155890 A1 | 7/2008 | Oyler | |
| 2009/0088757 A1 | 4/2009 | Tulkis | |
| 2009/0151240 A1 | 6/2009 | Kayama et al. | |
| 2009/0285642 A1 | 11/2009 | De Greef | |
| 2010/0028505 A1 | 2/2010 | Katzke et al. | |
| 2010/0041095 A1 | 2/2010 | Zeikus | |
| 2010/0116986 A1 | 5/2010 | Obuki et al. | |
| 2010/0151558 A1 | 6/2010 | Alianell et al. | |
| 2010/0162620 A1 | 7/2010 | McCaffrey et al. | |
| 2010/0281836 A1 | 11/2010 | Vanhoute et al. | |
| 2010/0325948 A1 | 12/2010 | Parsheh et al. | |
| 2011/0016773 A1 | 1/2011 | Nichols et al. | |
| 2011/0092726 A1 | 4/2011 | Clarke | |
| 2011/0172102 A1 | 7/2011 | Jacob et al. | |
| 2012/0009660 A1 | 1/2012 | Pottathil et al. | |
| 2012/0110901 A1* | 5/2012 | Olivier | A23K 20/163 44/605 |
| 2012/0117869 A1 | 5/2012 | Javan et al. | |
| 2012/0171753 A1 | 7/2012 | Ivry | |
| 2012/0288917 A1 | 11/2012 | Krenbrink et al. | |
| 2012/0308989 A1 | 12/2012 | Barclay et al. | |
| 2013/0023044 A1 | 1/2013 | Gleason | |
| 2013/0183705 A1 | 7/2013 | Barclay et al. | |
| 2013/0192130 A1 | 8/2013 | Eckelberry | |
| 2013/0244309 A1 | 9/2013 | Singh et al. | |
| 2014/0023675 A1 | 1/2014 | Lina et al. | |
| 2014/0212955 A1 | 7/2014 | Ploechinger | |
| 2014/0221630 A1 | 8/2014 | Olivier et al. | |
| 2014/0338261 A1 | 11/2014 | Sykes | |
| 2014/0356496 A1 | 12/2014 | Mulnyczuk | |
| 2015/0072400 A1 | 3/2015 | Clarke | |
| 2015/0275161 A1 | 10/2015 | Gressel et al. | |
| 2016/0030350 A1 | 2/2016 | Muller | |
| 2016/0288001 A1 | 10/2016 | Johnson | |
| 2016/0360715 A1 | 12/2016 | Sherlock et al. | |
| 2017/0223935 A1 | 8/2017 | Behrens | |
| 2018/0014486 A1 | 1/2018 | Creechley et al. | |
| 2018/0118595 A1 | 5/2018 | Curry | |

FOREIGN PATENT DOCUMENTS

| | | | |
|---|---|---|---|
| CN | 101370574 A | 2/2009 | |
| CN | 101595943 | 12/2009 | |
| CN | 102448286 | 5/2012 | |
| CN | 103002752 A | 3/2013 | |
| CN | 202960947 | 6/2013 | |
| CN | 202960947 U | 6/2013 | |
| CN | 104126494 | 11/2014 | |
| CN | 104126494 A | 11/2014 | |
| CN | 204092345 | 1/2015 | |
| CN | 104413257 | 3/2015 | |
| CN | 104585067 A | 5/2015 | |
| DE | 4133920 | 11/1993 | |
| EP | 0285195 | 10/1988 | |
| EP | 0639329 A1 * | 2/1995 | A01N 37/44 |
| EP | 0765599 | 4/1997 | |
| FR | 2522479 | 9/1983 | |
| JP | S52151199 | 12/1977 | |
| JP | 54-73148 | 6/1979 | |
| JP | S54147650 | 11/1979 | |
| JP | S56-031425 | 3/1981 | |
| JP | 359-183635 A | 10/1984 | |
| JP | 2001502918 | 3/2001 | |
| JP | 2001-346544 | 12/2001 | |
| JP | 2002-306147 A | 10/2002 | |
| JP | 2002-532112 A | 10/2002 | |
| JP | 2004097021 | 4/2004 | |
| JP | 2005007837 | 1/2005 | |
| JP | 2005065626 A | 3/2005 | |
| JP | 2008-043207 A | 2/2008 | |
| JP | 2010-214278 A | 9/2010 | |
| JP | 2011-019508 A | 2/2011 | |
| JP | 2011254724 | 12/2011 | |
| JP | 2013521808 A | 6/2013 | |
| KR | 20000018164 U | 10/2000 | |
| KR | 101153379 | 6/2012 | |
| MX | 2011010995 | 1/2012 | |
| NL | 20111038645 | 9/2012 | |
| WO | 9105849 | 5/1991 | |
| WO | 9818344 | 5/1998 | |
| WO | 9145523 | 6/2001 | |
| WO | 2002034755 | 5/2002 | |
| WO | 03028432 | 4/2003 | |
| WO | 2007109066 | 9/2007 | |
| WO | 2007111677 | 10/2007 | |
| WO | 2008020457 | 2/2008 | |
| WO | 2008033573 | 3/2008 | |
| WO | 2010123943 | 10/2010 | |
| WO | 2010144877 | 12/2010 | |
| WO | 2011044194 | 4/2011 | |
| WO | 2011116252 | 9/2011 | |
| WO | WO2011116252 | 9/2011 | |
| WO | 2011-156662 A2 | 12/2011 | |
| WO | 2011156662 | 12/2011 | |
| WO | 2014046543 | 3/2014 | |

(56) References Cited

FOREIGN PATENT DOCUMENTS

OTHER PUBLICATIONS

Freidig et al., Variation in Oxalic Acid Content among Commercial Table Beet Cultivars and Related Crops. Journal of the American Society for Horticultural Science, vol. 136, No. 1, pp. 54-60 (2011).
Extended Search Report in European Patent Application No. 16835862.0, dated Nov. 9, 2018.
Mazen, Ahmed M.A., "Calcium oxalate formation in Lemna minor: physiological and ultrastructural aspects of high capacity calcium sequestration" New Phytologist vol. 161, pp. 435-448, 2003.
Extended Search Report in European Patent Application No. 16845285.2 dated Jan. 15, 2019.
Watson, Elaine, "Ultra-fast-growing aquatic plant promises year-round supply of sustainable vegetable protein", Jul. 24, 2015, p. 1-4, XP055537613, www.bakeryandsnacks.com, Retrieved from Internet: URL: www.bakeryandsnacks.com/Article/2015/07/06/Aquatic-plant-promises-year-round-supply-of-sustainable-plant-protein. [Retrieved from ntemet on Dec. 21, 2018].
Extended Search Report in European Patent Application No. 16808454.9 dated Feb. 6, 2019.
Kwag, J.H. et al. "Conditions for artificial culture of Lemna Paucicostata and potentiality as an alternative biomass source"; J.Lives.House & Env. 16 (2) pp. 143-152, 2010.
First Examination Report in Australian Patent Application No. 2016276974, dated Apr. 9, 2019.
Partial Supplementary European Search Report in European Patent Application No. 16808454.9 dated Nov. 11, 2018.
International Preliminary Report on Patentability by the International Preliminary Examination Authority (Korean Intellectual Property Office) in International Application No. PCT/US2016/051380, dated Mar. 13, 2018.
International Preliminary Report on Patentability by the International Preliminary Examination Authority (Koean Intellectual Property Office) in PCT/US2016/051366, dated Mar. 22, 2018.
International Search Report and Written Opinion of the International Searching Authority (Korean Intellectual Property Office) in International Application No. PCT/US2016/051366, dated Dec. 22, 2016.
International Search Report and Written Opinion of the International Searching Authority (Korean Intellectual Property Office) in International Application No. PCT/US2016/051380, dated Dec. 26, 2016.
Mutiara, Titi K., et al., 'Effect of blanching treatments against protein content and amino acid drumstick leaves (*Moringa oleifera*)', Journal of Food Research, vol. 2, No. 1, pp. 101-108 (2013).
Schaafsma, Gertjan, 'Advantages and limitations of the protein digestibility-corrected amino acid score (PDCAAS) as a method for evaluating protein quality in human diets', British Journal of Nutritiion, vol. 108, pp. S333-S336 (2012).
Cheng et al., "Growing Duckweed to Recover Nutrients from Wastewaters and for Production of Fuel Ethanol and Animal Feed", Clean, vol. 37, No. 1, pp. 17-26 (2009).
Freidig et al., Variation in Oxalic Acid Content among Commercial Table Beet Cultivars and Related Crops. Journal of the American Society for Horticultural Science, vol. 136, No. 1, pp. 54-60 (2011).
International Search Report and Written Opinion of the International Searching Authority (Korean Intellectual Patent Office) for corresponding PCT application No. PCT/US2016/04642,2 dated Nov. 10, 2016.
International Preliminary Report on Patentability by the International Preliminary Examination Authority (Korean Intellectual Patent Office) for corresponding PCT application No. PCT/US2016/046422, dated Feb. 22, 2018.
Examination Report, mailed in related Chinese Patent Application No. 201080023569.X, dated Sep. 20, 2012.
Office Action, mailed in Brazilian Patent Application No. PI1015000-5, notification published Jan. 23, 2018.
Office Action mailed in Brazilian Patent Application No. PI1015000-5, dated Dec. 20, 2017.
International Search Report and Written Opinion of the International Searching Authority (US) in related International Application No. PCT/US2010/031811, dated Jun. 18, 2010.
International Preliminary Report on Patentability of the International Preliminary Examination Authority (US) in related International Application No. PCT/US2010/031811, dated Oct. 11, 2011.
Office Action received in Brazilian Patent Application No. PI1015000-5, notification published May 10, 2018.
Office Action, mailed in Chinese Patent Application No. 201610789415.0 dated Nov. 5, 2018.
International Search Report and Written Opinion of the International Searching Authority (US) in PCT International Application No. PCT/US2011/028911, dated Nov. 30, 2011.
Office Action in Mexican Patent Application No. MX/a/2014/010053, dated Feb. 13, 2017.
Office Action mailed in Malaysian Patent Application No. PI 2011005000 dated Jun. 30, 2015.
Extended Search Report in European Patent Application No. 11757038.2, dated Mar. 9, 2017.
Office Action in European Patent Application No. 11757038.2, dated Jul. 16, 2018.
Office Action in Australian Patent Application No. 2015255285, dated Mar. 3, 2017.
Preliminary Examination Report in Peruvian Patent Application No. 1563-2012, dated Apr. 17, 2017.
International Preliminary Report on Patentability of the International Preliminary Examination Authority in PCT International Application No. PCT/US2011/028911, dated Sep. 18, 2012.
Office Action in Canadian Patent Application No. 2793512, dated Mar. 28, 2018.
Office Action in Canadian Patent Application No. 2793512, dated Aug. 7, 2017.
Office Action in Indonesian Patent Application No. W00201204170, dated Sep. 29, 2017.
Office Action in Japanese Patent Application No. 2015-020932 dated Jan. 27, 2017.
Office Action in Japanese Patent Application No. 2015-020932 dated Dec. 5, 2017.
Office Action in Indian Patent Application No. 8902/DELNP/2012 dated Aug. 3, 2018.
Office Action in European Patent Application No. 11757038.2, dated Jan. 3, 2019.
International Preliminary Report on Patentability by the International Preliminary Examination Authority for International Application No. PCT/US2016/037097, dated Dec. 22, 2017.
International Search Report and Written Opinion of the International Searching Authority for PCT application No. PCT/US2016/037099, dated Oct. 5, 2016.
International Preliminary Report on Patentability by the International Preliminary Examination Authority (Korean Intellectual Patent Office) for International Application No. PCT/US2016/037099, dated Dec. 12, 2017.
Extended Search Report in European Patent Application No. 16808483.8, dated Dec. 21, 2018.
International Preliminary Report on Patentability by the International Preliminary Examination Authority (Korean Intellectual Property Office) for International Application No. PCT/US2016/037046, dated Dec. 12, 2017.
International Preliminary Report on Patentability by the International Preliminary Examination Authority (Korean Intellectual Property Office) for International Application No. PCT/US2016/041156, dated Jan. 18, 2018.
International Search Report and Written Opinion of the International Searching Authority (Korean Intellectual Property Office) for corresponding PCT application No. PCT/US2016/046422, dated Nov. 10, 2016.
International Preliminary Report on Patentability by the International Preliminary Examination Authority (Korean Intellectual Property Office) for International Application No. PCT/US2016/046422, dated Feb. 22, 2018.

(56) References Cited

OTHER PUBLICATIONS

International Search Report and Written Opinion of the International Searching Authority (Korean Intellectual Property Office) for International Application No. PCT/US2016/037097, dated Sep. 12, 2016.
Supplementary European Search Report in European Patent Application No. 16808482.0, dated Feb. 21, 2019.
Sogbesan, OA; "Utilization of Treated Duckweed Meal (*Lemna pausicostata*) as Plant Protein Supplement in African Mud Catfish (*Clarias gariepinus*) Juvenile Diets" Fisheries and Aquaculture Journal, vol. 6, Issue 4, ISSN: 2150-3508 FAJ, 2015.
Extended Search Report of European Patent Office in European Patent Application No. 16845295.1, dated Jan. 15, 2019.
Office Action, mailed in Indian Patent Application No. 8948/DELNP/2011 dated Apr. 11, 2018.
Office Action, mailed in Brazilian Patent Application No. PI1015000-5, dated Sep. 26, 2018.
Pedroni et al., A Proposal to Establish International Network on Biofixation of C02 and Greenhouse Gas Abatement with Microalgae, Journal of Energy and Environmental Research, vol. 1, No. 1, Nov. 2001.
Hallam, Murray, Practical Aquaponics for Everyone. Retrieved from Internet: URL: www.aquaponics.net.au/sites1 O.html, Wayback Machine publication dated Dec. 2008, 3 pages.
The Garden Pond Blog. Retrieved from Internet: URL: jeremybiggs.wordpress.com/2008/10/28/duck-attack/, publication Oct. 2008, 2 pages.
Workshop to produce an Information Kit on Farmer-proven integrated agriculture-aquaculture technologies, IIRR; Retrieved from Internet: collections.infocollections.org/ukedu/en/d/Jii23we/9.1.html, 1992, 10 pages.
Fasakin, E.A. "Nutrient quality of leaf protein concentrates produced from water fern {*Azolla africanna* Desv) and Duckweed {*Spirodela polyrrhiza* L. Schleiden)", Bioresource Technology., vol. 69, No. 2, Aug. 1, 1999 {Aug. 1, 1999), pp. 185-187.
Fowden, L. "The Composition of the Bulk Proteins of Chlorella" [online] Published Jun. 20, 1951. Retrieved fromInternet Jun. 1, 2017: <URL:https://www.ncbi.nlm.nih.gov/pmc/articles/PMC1197660/pdf/biochemj00910-0079.pdf>.
Bolenz, S. et al. "Treatments of Water Hyacinth Tissue to Obtain Useful Products", Biological Wastes, Amsterdam, NL, vol. 33, No. 4, Jan. 1, 1990 {Jan. 1, 1990), pp. 263-274.
Kindel, Paul K. et al. "Solubilization of pectic polysaccharides from the cell walls of Lemna minor and Apium graveolens", Phytochemistry, vol. 41, No. 3, Feb. 1, 1996 {Feb. 1, 1996), GB, pp. 719-723.
Byers, M. "The Amino Acid Composition of Some Leaf Protein Preparations" in IBP Handbook No. 20, Leaf Protein: Its agronomy, Preparation, Quality and Use. 1971, International Biological Programme pp. 95-115.
Kennedy, David "Leaf Concentrate: A Field Guide for Small Scale Programs". Leaf for Life, 1993.
International Search Report and Written Opinion of the International Searching Authority for PCT application No. PCT/US2016/037046, dated Oct. 27, 2016.
International Search Report and Written Opinion of the International Searching Authority (Korean Intellectual PatentOffice) for International Application No. PCT/US2016/041156, dated Oct. 18, 2016.
Office Action dated Jan. 6, 2020 in Chinese Patent Application No. CN201680047105.X.
Office Action dated Feb. 19, 2020 in Australian Patent Application No. AU2016275066.
Office Action dated Aug. 21, 2020 in Chinese Application No. 201680065224.8.
Office Action dated Jul. 3, 2020 in Chinese Application No. 201680047237.2.
Office Action dated Jul. 9, 2020 in Japanese Application No. 2018-516402.
Office Action dated Aug. 4, 2020 in Japanese Application No. 2018-506982.
Office Action dated Jun. 24, 2020 in European Application No. 16845295.1.
Office Action dated Jun. 23, 2020 in Japanese Application No. 2018-532531.
Annual Review of Plant Biology, 2005, vol. 56, p. 41-71.
Sogbesan et al, "Utilization of Treated Duckweed Meal (*Lemna pausicostata*) as Plant Protein Supplement in African Mud Catfish (*Clarias gariepinus*) Juvenile Diets", Fisheries and Aquaculture Journal, vol. 06, No. 04, Jul. 12, 2015, p. 1-5, XP055535965.
Office Action dated Nov. 12, 2020 in European Patent Application No. 16808482.0.
Lentein, "Clean. Green. Protein", Retrieved from: https://web.archive.org/web/20150901074209/https://lentein.com, web accessed on Jul. 17, 2020.
Lentein, "Green Protein Powder", Retrieved from: https://web.archive.org/web/20150822012645/https://lentein.com/lentein-plus-powder, web accessed on Jul. 17, 2020.
Office Action, mailed in Japanese Patent Application No. 2018-516396, dated Jun. 2, 2020.
Office Action, mailed in Japanese Patent Application No. 2018-516401, dated Jun. 2, 2020.
Office Action, mailed in Japanese Patent Application No. 2018-532528, dated Jun. 23, 2020.
Office Action dated Dec. 14, 2020 in Chinese Application No. 201680058494.6.
Office Action dated Sep. 2, 2020 in Chinese Application No. 201680047105.x.
Office Action dated Dec. 3, 2020 in Chinese Application No. 201680047175.5.
Kammerer, Dietmar Rolf, Chapter 11—Resin Adsorption and Ion Exchange to Recover and Fractionate Polyphenols, Polyphenols in Plants, 219-230, (2014).
Office Action dated Nov. 17, 2020 in Brazilian Patent Application No. BR112018004808-9 (agent's reporting letter).
Mazen, Ahmed M. A., et al., Calcium oxalate formation in Lemna minor: physiological and ultrastructural aspects of high capacity calcium sequestration. New Phytologist (2003), 435-448.
Extended European Search Report dated Feb. 26, 2021 in European Patent Application No. 20197495.3.
Office Action dated May 28, 2021 in Australian Patent Application No. 2016276972.
Notice of Acceptance dated May 12, 2021 in Australian Patent Application No. 2016321425.
Office Action dated May 24, 2021 in Australian Patent Application No. 2020201808.
Office Action dated Jun. 18, 2021 in Chinese Patent Application No. 201680065224.8.
Office Action dated Apr. 27, 2021 in Japanese Patent Application No. 2018-532528.
Examination Report dated Dec. 7, 2020 in European Patent Application No. 16845285.2.
Stuart L. Cantor: "New Plant Protein Powerhouses Prepared Foods", Sep. 11, 2015, XP055755579.
Titi Mutiara Kirana et al. "Effect of Blanching Treatments Against Protein Content and Amino Acid Drumstick Leaves (*Moringa oleifera*)", Journal of Food Research, vol. 2, No. 1, Jan. 1, 2013, pp. 101-108, XP055367771.
Examination Report dated Dec. 17, 2020 in Australian Patent Application No. 2016321414.

\* cited by examiner

METHODS AND SYSTEMS FOR EXTRACTING REDUCED OXALIC ACID PROTEIN FROM AQUATIC SPECIES AND COMPOSITIONS THEREOF

CROSS-REFERENCE TO RELATED APPLICATIONS

This application is a U.S. National Stage Entry of International Application No. PCT/US2016/046422 filed on Aug. 10, 2016, which claims priority to U.S. Provisional Patent Application No. 62/203,199 filed on Aug. 10, 2015. The contents of the above applications are hereby incorporated in their entirety by reference.

FIELD OF THE DISCLOSURE

The present disclosure relates, in some embodiments, to compositions, methods and systems for producing proteins from an aquatic species (e.g., *Lemna*) with reduced (e.g., ≤0.6%, ≤0.05%) oxalic acid content and compositions thereof. In some embodiments, the present disclosure relates to compositions of a microcrop protein product having a reduced oxalic acid content.

BACKGROUND OF THE DISCLOSURE

An ever-increasing global population continues to fuel a plethora of sustainability concerns including sufficient and affordable access to protein sources for both feed animals and human consumption, particularly in developing nations. While marine protein sources are often utilized in feeds due to their desirable nutritional profile and enhanced palatability, high production costs lead to an increased demand for alternatives. However, many plant species are unsuitable alternatives due to their inferior amino acid profile and/or high fiber content. And many practices for extracting protein from alternative protein sources yield products with protein integrity, solubility, and/or dispersibility characteristics that are unsuitable for many human consumption and animal feed applications. Additionally, some practices for extracting protein from alternative protein sources yield products with increased content of anti-nutritional components, such as oxalic acid, making them undesirable for many human consumption applications. Furthermore, water conservation concerns—particularly in equatorial and arid regions—are a driving factor in identifying suitable alternative species for the production of protein concentrates.

SUMMARY

Accordingly, a need has arisen for improved methods and systems for the production of a concentrated protein product with increased protein integrity, solubility, and/or dispersibility characteristics, as well as, reduced oxalic acid content. Further, a need has arisen for improved methods and systems for the production of concentrated proteins in a manner requiring decreased water and/or energy expenditures.

The present disclosure relates, according to some embodiments, to methods of treating a biomass comprising a microcrop (e.g., *Lemna*) to produce a product comprising soluble microcrop protein (e.g., *Lemna* protein concentrate) having a reduced oxalic acid content (e.g., wherein total oxalic acid content is ≤0.6% DMB, ≤0.05% DMB).

The present disclosure relates, in some embodiments, to a method of generating a soluble microcrop protein with the method including: lysing a biomass (e.g., *Lemna*) to form a lysed biomass; precipitating oxalate from the lysed biomass, separating the lysed biomass to generate a juice fraction and a solid fraction; separating the juice fraction to generate a first juice and a first cake; and filtering the first juice to generate a first soluble protein and a first reject stream. According to some embodiments, a first soluble protein may have an oxalic acid content of less than about 0.6% DMB (e.g., less than about 0.1% DMB, less than about 0.05% DMB).

In some embodiments, a method may further include filtering a first soluble protein to generate a second soluble protein and a second reject stream. According to some embodiments, a method may further include filtering a second soluble protein to generate a concentrated protein product and a permeate. A method, in some embodiments, may further include drying a concentrated protein product to generate a dry protein concentrate. According to some embodiments, a dry protein concentrate may have one or more of the following characteristics: a protein concentration of at least about 50% by weight, a solubility value of at least 50%, and/or a dispersibility value of at least 50%.

A method may further include, according to some embodiments, soaking a biomass in a second medium (e.g., having less than about 8 ppm of a calcium source, or less than about 4 ppm of a nitrogen source, or both) to form a soaked biomass. In some embodiments, a method may include buffering a soaked biomass in a third medium. According to some embodiments, a method may include precipitating oxalate from a juice fraction.

Additionally, the present disclosure relates to a method of generating a soluble microcrop protein with the method comprising: lysing a biomass (e.g., *Lemna*) to form a lysed biomass; separating the lysed biomass to generate a juice fraction and a solid fraction, precipitating oxalate from the juice fraction; separating the juice fraction to generate a first juice and a first cake; and filtering the first juice to generate a first soluble protein and a first reject stream. In some embodiments, a first soluble protein may have an oxalic acid content of less than about 0.6% DMB (e.g., less than about 0.1% DMB, less than about 0.05% DMB). A method, in some embodiments, may include precipitating oxalate from a lysed biomass.

In some embodiments, a method may include filtering a first soluble protein to generate a second soluble protein and a second reject stream. According to some embodiments, a method may include filtering a second soluble protein to generate a concentrated protein product and a permeate. A method, in some embodiments, may further comprise drying a concentrated protein product to generate a dry protein concentrate. According to some embodiments, a dry protein concentrate may have one or more of the following characteristics: a protein concentration of at least about 50% by weight, a solubility value of at least 50%, and/or a dispersibility value of at least 50%.

A method may include, according to some embodiments, soaking a biomass in a second medium (e.g., having less than about 8 ppm of a calcium source, or less than about 4 ppm of a nitrogen source, or both) to form a soaked biomass. In some embodiments, a method may include buffering a soaked biomass in a third medium.

The disclosure relates, in some embodiments, to a method of cultivating and treating a biomass comprising a microcrop (e.g., *Lemna*) to generate a product comprising a soluble microcrop protein with the method including: cultivating a microcrop in a first medium to form a biomass, harvesting the biomass, and extracting a soluble protein from the biomass. According to some embodiments, a first medium may include at least one of (i) a calcium; concentration of at least 20 ppm and (ii) one or more anti-photosynthetic dyes. In some embodiments, one or more anti-photosynthetic dyes may be selected from a disodium salt of (n-ethyl-n-[4-[[4-[ethyl[(3-sulfophenyl)methyl]amino]-phenyl](2-sulfophenyl)-methylene)]2,5-cyclohexadien-1-ylidene]-3-sulfobenzenemethanaminium hydroxide inner salt, a trisodium salt of (4E)-5-oxo-1-(4-sulfonatophenyl)-4-[(4-sulfonatophenyl) hydrazono]-3-pyrazolecarboxylate, diazanium; 2-[[4-[ethyl-[(3-sulfonatophenyl)methyl]amino]phenyl]-[4-[ethyl-[(3-sulfonatophenyl) methyl] azaniumylidene] cyclohexa-2,5-dien-1-ylidene] methyl] benzenesulfonate, benzyl-[4-[[4-[benzyl(ethyl)amino]phenyl]-(5-hydroxy-2,4-disulfophenyl)methylidene]cyclohexa-2,5-dien-1-ylidene]-ethylazanium, a disodium salt of 2-(1,3-dioxoinden-2-yl) quinoline-6,8-disulfonate, or combinations thereof. In some embodiments, a soluble protein may have an oxalic acid content of less than about 0.6% DMB (e.g., less than about 0.1% DMB, less than about 0.05% DMB).

According to some embodiments, a method may include lysing a biomass to form a lysed biomass, separating the lysed biomass to generate a juice fraction and a solid fraction, separating the juice fraction to generate a first juice and a first cake, and filtering the first juice to generate a first soluble protein and a first reject stream.

In some embodiments, a method may include filtering a first soluble protein to generate a second soluble protein and a second reject stream. According to some embodiments, a method may include filtering a second soluble protein to generate a concentrated protein product and a permeate. A method, in some embodiments, may further comprise drying a concentrated protein product to generate a dry protein concentrate. According to some embodiments, a dry protein concentrate may have one or more of the following characteristics: a protein concentration of at least about 50% by weight, a solubility value of at least 50%, and/or a dispersibility value of at least 50%.

A method, according to some embodiments, may include soaking a biomass in a second medium (e.g., having less than about 8 ppm of a calcium source, or less than about 4 ppm of a nitrogen source, or both) to form a soaked biomass. In some embodiments, a method may include buffering a soaked biomass in a third medium.

The present disclosure further relates to a soluble protein product from a biomass (e.g., *Lemna*) comprising a microcrop produced by a method described herein. According to some embodiments, a soluble protein product may have an oxalic acid content of less than 0.6% DMB (e.g., less than about 0.1% DMB, less than about 0.05% DMB). In some embodiments, a soluble protein product may be dried to generate a dry protein concentrate. According to some embodiments, a dry protein concentrate may have one or more of the following characteristics: a protein concentration of at least about 50% by weight, a solubility value of at least 50%, and/or a dispersibility value of at least 50%.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Some embodiments of the disclosure may be understood by referring, in part, to the present disclosure and the accompanying drawings, wherein.

DETAILED DESCRIPTION

Figure 1A:
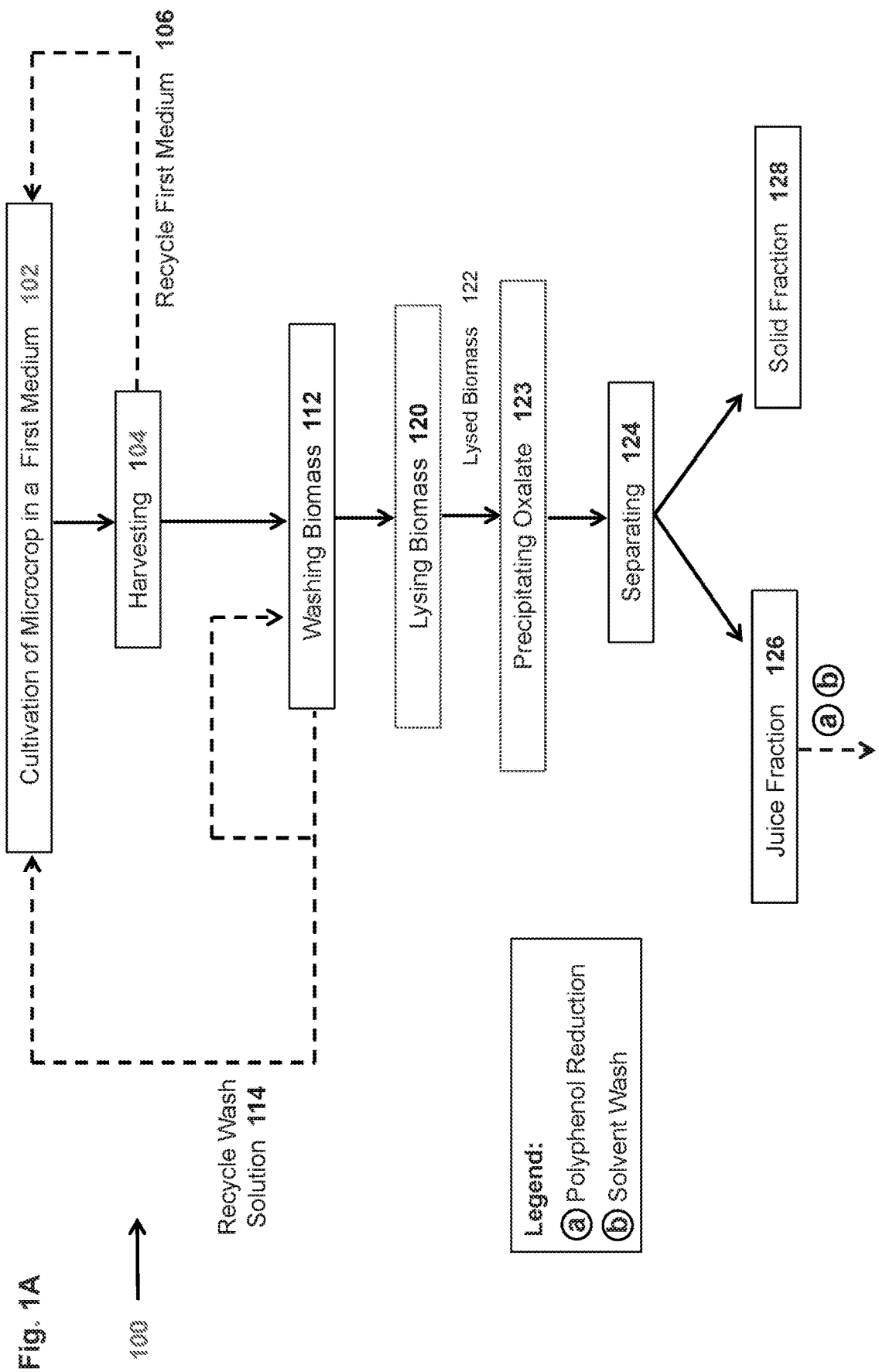
FIG. 1A is a flow diagram illustrating a system for cultivating, harvesting, and processing a microcrop for the production of a protein concentrate having a reduced oxalic acid content according to a specific example embodiment of the disclosure.

The present disclosure relates to compositions, systems, and methods for producing a protein concentrate (e.g., soluble protein, dry protein concentrate) having a reduced oxalic acid content (e.g., wherein total oxalic acid content is ≤0.6% DMB, ≤0.05% DMB) from a microcrop (e.g., aquatic plant species, *Lemna*, algal species). For example, a method may comprise growing, harvesting, and/or separating a microcrop (e.g., aquatic plant species, *Lemna*, algal species) for the production of protein concentrate (e.g., soluble protein, dry protein concentrate) having a reduced oxalic acid content according to specific example embodiments of the disclosure. A method, in some embodiments, may comprise extracting a soluble protein from a microcrop (e.g., aquatic plant species, *Lemna*, algal species) for the production of protein concentrate (e.g., soluble protein, dry protein concentrate) having a reduced oxalic acid content according to specific example embodiments of the disclosure.

Persons skilled in the art would understand that there are multiple methods of extracting a protein from a protein source (e.g., a microcrop, a biomass). In some embodiments, extracting a protein from a protein source may comprise disrupting (e.g., lysing) one or more cells of the protein source for example by chemical (e.g., detergents), biological (e.g., enzymes), thermal (e.g., freezing, thawing), and/or mechanical means (e.g., milling). Protease inhibitors may be employed wherein a protein being extracted is sensitive to proteolysis. In some embodiments, cell debris may be removed through means such as filtration and/or centrifugation. According to some embodiments, extracting a protein from a protein source may comprise precipitating a soluble protein from a solution (e.g., media), for example using methods of manipulating temperature (e.g., cooling or heating), aggregation agents (e.g., ammonium sulphates), reducing media volume (e.g., evaporation), centrifugation, filtration, or any combination thereof. In some embodiments, extracting a protein from a protein source may comprise purification strategies including chromatographic methods such as ion exchange chromatography, size exclusion chromatography, affinity chromatography, and high performance liquid chromatography.

A method may be performed, in some embodiments, in a series of steps, one or more of which may be repeated. For example, a method may comprise a single cycle (e.g., no step is repeated) resulting in the production of protein concentrate (e.g., soluble protein, dry protein concentrate) having a reduced oxalic acid content. In some embodiments, a method may comprise multiple cycles (e.g., first portion, second portion) or a continuous process for the production of protein concentrate (e.g., soluble protein, dry protein concentrate) having a reduced oxalic acid content such that products, intermediates and/or byproducts of an earlier cycle of the process may be recycled into one or more subsequent cycles of the process. One of ordinary skill in the art having the benefit of the present disclosure will appreciate that oxalic acid, if present, may be in its protonated ($H_2C_2O_4$ or HOOCCOOH) or deprotonated ($HC_2O_4^-$ or $C_2O_4^{2-}$) form. In some embodiments, oxalate (i.e., $C_2O_4^{2-}$) may be present in a salt form. For example, an oxalate salt may comprise sodium oxalate, potassium oxalate, calcium oxalate, ammonium oxalate, or combinations thereof. According to some embodiments, a microcrop may be Lemna.

Microcrop

In some embodiments, a microcrop may comprise a single aquatic species (e.g., Lemna species, Salvinia species). A microcrop may include species of Lemna (e.g., duckweed), Spirodela, Landoltia, Wolfiella, Salvinia (e.g., floating fern), Wolffia (e.g., watermeal), Azolla (e.g., mosquito fern), Pistia (e.g., water lettuce), or any combination thereof. According to some embodiments, a microcrop may be a species of Lemna, for example, Lemna minor, Lemna obscura, Lemna minuta, Lemna gibba, Lemna valdiviana, or Lemna aequinoctialis. A microcrop may comprise, according to some embodiments, a combination of two or more aquatic species. In some embodiments, a microcrop may be selected from a local aquatic species based on identified compositional and growth characteristics that have developed within the local environmental conditions. Local species may out-compete other species in open ponds or bioreactors based on their adaptation to the local environmental conditions. A microcrop, in some embodiments, may be adjusted in response to seasonal variations in temperature and light availability.

A microcrop may have characteristics that are advantageous in comparison to other aquatic species (e.g., rapid growth rate; reduced nutritional requirements; ease of harvesting and/or processing; enhanced amino acid profile; enhanced palatability; reduced evapotranspiration rate; increased protein composition, reduced oxalic acid content).

For example, Lemna is a genus of free-floating aquatic plants from the Lemnaceae family (e.g., duckweed) that grow rapidly. Lemna protein has an essential amino acid profile that more closely resembles animal protein than most other plant proteins. Table 1 shows a typical essential amino acid compositional profile of Lemna protein. Additionally, Lemna provides high protein yields, with freshly harvested Lemna containing up to about 43% protein by dry weight. Furthermore, compared with most other plants, Lemna leaves have a low fiber content (e.g., about 5%-about 15% in dry matter) and are highly digestible, even for monogastric animals. This contrasts with the compositions of many crop species (e.g., soy beans, rice, maize) which have fiber contents of approximately 50% and low digestibility.

TABLE 1

Essential Amino Acid Profile of Lemna Protein Concentration

| Essential Amino Acid | Protein (g/100 g) |
|---|---|
| Lysine | 5.9 |
| Leucine | 9.7 |
| Isoleucine | 5.1 |
| Methionine | 2.4 |
| Phenylalanine | 6.3 |
| Threonine | 4.4 |
| Tryptophan | 2.0 |
| Valine | 6.3 |
| Histidine | 2.7 |
| Arginine* | 6.8 |

*Conditionally non-essential amino-acid.

Cultivation of a Microcrop

In some embodiments a microcrop may be asexually propagated (e.g., cultivated) by contacting the microcrop with a first medium (e.g., an aqueous nutrient composition, a growth medium) under conditions that permit expansion. A microcrop may be cultivated in a bioreactor system, according to some embodiments (e.g., 102). A bioreactor system may contain a first medium (e.g., a growth medium) comprising water and/or a nutrient composition, according to some embodiments. A nutrient composition, in some embodiments, may include at least one of nitrogen, phosphorus, potassium, and calcium. In some embodiments, a first medium may comprise dissolved gaseous oxygen and/or dissolved gaseous carbon dioxide. According to some embodiments, a first medium may be configured to have an increased calcium composition (e.g., an increased calcium growth medium). For example, an increased calcium first medium may comprise a calcium concentration of ≥about 120 parts per million (ppm), or ≥about 115 ppm, or ≥about 110 ppm, or ≥about 105 ppm, or ≥about 100 ppm, or ≥about 95 ppm, or ≥about 90 ppm, or ≥about 85 ppm, or ≥about 80 ppm, or ≥about 75 ppm, or ≥about 70 ppm, or ≥about 65 ppm, or ≥about 60 ppm, or ≥about 55 ppm, or ≥about 50 ppm, or ≥about 45 ppm, or ≥about 40 ppm, or ≥about 35 ppm, or ≥about 30 ppm, or ≥about 25 ppm, or ≥about 20 ppm, where "about" in this sentence includes ±10% of the indicated concentration. In some embodiments, an increased calcium first medium may comprise a calcium concentration of about 20 ppm to about 120 ppm, or about 25 ppm to about 120 ppm, or about 30 ppm to about 120 ppm, or about 40 ppm to about 120 ppm, or about 50 ppm to about 120 ppm, or about 60 ppm to about 120 ppm, or about 70 ppm to about 120 ppm, or about 80 ppm to about 120 ppm, or about 20 ppm to about 100 ppm, or about 30 ppm to about 100 ppm, or about 40 ppm to about 100 ppm, or about 50 ppm to about 100 ppm, or about 60 ppm to about 100 ppm, or about 70 ppm to about 100 ppm, or about 80 ppm to about 100 ppm. An increased calcium first medium, according to some embodiments, may comprise a calcium concentration of at least about 20 ppm (e.g., ±10%). In some embodiments an increased calcium first medium comprises at least about 100 ppm calcium. A bioreactor system may be configured to insert additional nutrients (e.g., nitrogen, phosphorus, potassium, calcium) or gases (e.g., oxygen, carbon dioxide, nitrogen) into the first medium at specified time indicators or in response to sensor readings. In some embodiments, a calcium may comprise calcium, calcium carbonate, calcium oxalate, calcium oxide, calcium citrate, calcium carbide, calcium phosphate, calcium sulfate, calcium chloride, or combinations thereof.

In some embodiments, a first medium may comprise one or more anti-photosynthetic dyes that are configured to attenuate photosynthetically active radiation within the growth medium. The one or more anti-photosynthetic dyes may be added at a sufficient volume or concentration to inhibit growth of at least one other aquatic organism (e.g., submerged aquatic species, phytoplankton, phytoalgae, epiphytic algae), according to some embodiments. An anti-photosynthetic dye may include at least one of (n-ethyl-n-[4-[[4-[ethyl[(3-sulfophenyl)methyl]amino]-phenyl](2-sulfophenyl)-methylene)]2,5-cyclohexadien-1-ylidene]-3-sulfobenzenemethanaminium hydroxide inner salt, disodium salt, (Colour Index Acid Blue 9 (Ref. No. 42090)), trisodium (4E)-5-oxo-1-(4-sulfonatophenyl)-4-[(4-sulfonatophenyl)hydrazono]-3-pyrazolecarboxylate (Colour Index Acid Yellow 23 (Ref. No. 19140)), diazanium; 2-[[4-[ethyl-[(3-sulfonatophenyl)methyl]amino]phenyl]-[4-[ethyl-[(3-sulfonatophenyl) methyl] azaniumylidene] cyclohexa-2,5-dien-1-ylidene]methyl] benzenesulfonate (Colour Index Acid Blue 34 (Ref. No. 42645)); benzyl-[4-[[4-[benzyl(ethyl)amino]phenyl]-(5-hydroxy-2,4-disulfophenyl) methylidene]cyclohexa-2,5-dien-1-ylidene]-ethylazanium (Colour Index Acid Blue 5 (Ref. No. 42052)); disodium-2-(1,3-dioxoinden-2-yl)quinoline-6,8-disulfonate (Colour Index Acid Yellow 3 (Ref. No. 15985)), and a mixture of (n-ethyl-n-[4-[[4-[ethyl[(3-sulfophenyl)methyl]amino]-phenyl](2-sulfophenyl)-methylene)]2,5-cyclohexadien-1-ylidene]-3-sulfobenzenemethanaminium hydroxide inner salt, disodium salt and trisodium (4E)-5-oxo-1-(4-sulfonatophenyl)-4-[(4-sulfonatophenyl)hydrazono]-3-pyrazolecarboxylate (Aquashade®). Other suitable anti-photosynthetic dyes may be found in Tables I and II of U.S. Pat. No. 4,042,367 to Wilson, which is incorporated herein by reference.

A first medium (e.g., an aqueous nutrient composition) may be provided in and/or added to a bioreactor (e.g., a pond) and may be maintained at a desired set-point level (e.g., specific volume), according to some embodiments. A bioreactor system, in some embodiments, may be configured to collect rainfall and/or to intake water from a source of ground, surface, or recycled water (e.g., storm water, recycled water) or any other suitable water source. According to some embodiments, a bioreactor system may further comprise an additional storage container (e.g., container or pond) for excess growth medium.

In some embodiments, one or more smaller bioreactors (e.g., pond) may be designed and sized to adequately serve as "feeder" bioreactors to a larger bioreactor. Smaller bioreactors, in some embodiments, may be first inoculated and grown to high density at which point they may optimally seed a larger bioreactor in a manner that supports faster growth.

In some embodiments, a bioreactor system may comprise a monitoring system. A monitoring system may be configured to display and/or provide one or more user alerts regarding bioreactor condition(s) (e.g., nutrient concentrations, pH, dissolved oxygen levels, growth medium levels, microcrop distribution, flow rate, temperature) and/or adjust operating conditions (e.g., growth medium flow rate and/or timing and/or quantity of nutrient addition; "feeder" microcrop addition, oxygen or carbon dioxide addition), in some embodiments. Adjustments may be made continuously, semi-continuously, periodically, intermittently, as needed, at set or variable times, or any other interval. In some embodiments, adjustments may be selected to optimize growth rates and/or yield of the aquatic species. For example, a microcrop species may be grown in large-scale, open bioreactors with monitoring systems configured to adjust the introduction of materials (e.g., fresh or recycled water, fresh or recycled growth media) based on, for example, exposure to light, which may thereby regulate nutrient consumption rates.

A bioreactor system may comprise, in some embodiments, a single container in which the microcrop may be cultivated. In some embodiments, the bioreactor system may comprise multiple cultivation containers that may be connected, partially connected, or disconnected. A bioreactor (e.g., a pond), in some embodiments, may be an earthen basin with the embankments made of compacted dirt removed from the interior bottom of the bioreactor. According to some embodiments the bioreactor may be an artificial container (e.g., metal, plastic, resin). A bioreactor system may comprise an open bioreactor, a closed bioreactor, a semi-open bioreactor, or any combination thereof. In some embodiments, a bioreactor system may be configured to divide the container(s) into channels or cells. A bioreactor system may be configured to permit a flow of growth medium, in some embodiments. A bioreactor system, in some embodiments, may include a propulsion system (e.g., paddle wheels, bubbling, submerged or surface water jets, submerged mixers) and/or a recirculation system. In some embodiments, a bioreactor system may be configured to adjust the flow rate of a growth medium (e.g., to redistribute nutrient concentrations or microcrop growth patterns).

In some embodiments a bioreactor system may be open (e.g., in a horizontal plane relative to the ground) of a bioreactor container (e.g., serpentine raceway) such that a growth medium contained within the bioreactor container and/or a microcrop growing on a top surface of the growth medium may be exposed to a wind initiating from an exterior of the bioreactor container. A bioreactor system, according to some embodiments, may be partially open (e.g., in a horizontal plane relative to the ground) with at least 90% or at least 80%, or at least 70%, or at least 60%, or at least 50%, or at least 40%, or at least 30%, or at least 20%, or at least 10% of the top surface of the contained culture media being open. A top surface may be open, according to some embodiments, where the surface is substantially free (e.g., free) of any covering or other barrier, where the surface is directly exposed to ambient weather conditions, where there is substantially no membrane, glass, cover or other barrier (whether or not such barrier has pores or apertures) between the surface and the atmosphere, and/or where ambient atmosphere is the only occupant of the space immediately and directly above the surface for a distance of at least about 1 meter above the surface.

A bioreactor system, in some embodiments, may monitor and adjust a thickness and distribution of a microcrop mat. For example, when a microcrop reaches a specified thickness or distribution a bioreactor system may initiate harvest procedures. In some embodiments, a minimum thickness of a microcrop mat may be maintained such that a desired evapotranspiration rate of a growth medium within a bioreactor system may be maintained. A minimum thickness of a microcrop may be maintained, in some embodiments, such that less sunlight is capable of penetrating a surface of a growth medium (i.e., reducing a growth potential of submerged aquatic species such as algae).

Harvesting of a Microcrop

A microcrop may be harvested in whole or in part at any desired time(s). For example, a microcrop may be harvested at one or more specific times, at regular or irregular intervals and/or continuously. Selection of harvest time(s) and/or intervals may be based on environmental conditions (e.g., precipitation, relative humidity, temperature range, average, low or high threshold and/or light intensity, wavelength range, duration of exposure) and/or the microcrop exhibiting one or more desired characteristics (e.g., mat thickness, mat distribution, maturation). Harvesting a microcrop may be manual or automated. In some embodiments, an automated skimmer system may collect a microcrop from a bioreactor system and transfer a harvested microcrop (e.g., via a pumping system) onto an inclined vibrating screen to separate a biomass from growth medium and debris. A microcrop, in some embodiments, may be harvested by vacuum skimming the microcrop from the bioreactor system through a stationary or mobile screen filter. According to some embodiments, a biomass slurry, including a harvested microcrop (e.g., *Lemna*) and a growth medium (e.g., water), may be conveyed to an inclined vibrating screen where a biomass (e.g., microcrop) may be separated from the first medium.

During harvesting, a separated first medium may be recycled back into a bioreactor system or to an additional storage container (e.g., container or pond), according to some embodiments (e.g., 106). In some embodiments, at least about 40%, or at least about 50%, or at least about 60%, or at least about 70%, or at least about 80%, or at least about 90%, or at least about 95% of a growth medium (e.g., water) separated from a biomass may be recycled for further use in cultivating, harvesting, and/or processing a microcrop.

Soaking and/or Buffering a Biomass

After harvesting, a biomass may be soaked (e.g., 108) and/or buffered (e.g., 110). Soaking and/or buffering a harvested biomass may contribute to a reduction in an oxalic acid content of a protein product. In some embodiments, soaking and/or buffering a harvested biomass may contribute to a reduction in an oxalic acid and/or oxalate content of a protein product.

In some embodiments, a harvested biomass may be soaked in a second medium (e.g., 108). A second medium may comprise water (e.g., ground water, surface water, recycled water), distilled water, reverse osmosis or nanofiltered water, and/or a nutrient composition, according to some embodiments. In some embodiments, a second medium may comprise any desired portion of recycled fluid. For example, a second medium may comprise at least about 10% (v/v), at least about 20% (v/v), at least about 30% (v/v), at least about 40% (v/v), at least about 50% (v/v), at least about 60% (v/v), at least about 70% (v/v), at least about 80% (v/v), or at least about 90% (v/v) recycled fluid from another stage of the process (e.g., a reject stream from filtration 260, 254).

According to some embodiments, a second medium may be configured to have a low nitrogen composition (e.g., a low nitrogen second medium). For example, a low nitrogen second medium may comprise a nitrogen concentration of ≤about 20 parts per million (ppm), ≤about 18 ppm, ≤about 16 ppm, or ≤about 14 ppm, or ≤about 12 ppm, or ≤about 10 ppm, or ≤about 9 ppm, or ≤about 8 ppm, or ≤about 7 ppm, or ≤about 6 ppm, or ≤about 5 ppm, or ≤about 4 ppm, or ≤about 3 ppm, or ≤about 2 ppm, or ≤about 1 ppm, or ≤about 0.5 ppm, or about 0 ppm. In some embodiments, a low nitrogen second medium may comprise a nitrogen concentration of about 0 ppm to about 20 ppm, or about 0.5 ppm to about 20 ppm, or about 0.5 ppm to about 15 ppm, or about 0.5 ppm to about 10 ppm, or about 1 ppm to about 9 ppm, or about 1 ppm to about 7 ppm, or about 1 ppm to about 6 ppm, or about 1 ppm to about 5 ppm, or about 3 ppm to about 6 ppm, or about 2 ppm to about 8 ppm. A low nitrogen second medium, according to some embodiments, may comprise a nitrogen concentration of at most about 10 ppm (e.g., ±1 ppm). In some embodiments, a low nitrogen second medium may comprise a nitrogen concentration of at most about 5 ppm (e.g., ±0.5 ppm).

According to some embodiments, a second medium may be configured to have a low calcium composition (e.g., a low calcium second medium). For example, a low calcium second medium may comprise a calcium concentration of ≤about 20 ppm, ≤about 18 ppm, ≤about 16 ppm, or ≤about 14 ppm, or ≤about 12 ppm, or ≤about 10 ppm, or ≤about 9 ppm, or ≤about 8 ppm, or ≤about 7 ppm, or ≤about 6 ppm, or ≤about 5 ppm, or ≤about 4 ppm, or ≤about 3 ppm, or ≤about 2 ppm, or ≤about 1 ppm, or ≤about 0.5 ppm, or about 0 ppm. In some embodiments, a low calcium second medium may comprise a calcium concentration of about 0 ppm to about 20 ppm, or about 0.5 ppm to about 20 ppm, or about 0.5 ppm to about 15 ppm, or about 0.5 ppm to about 10 ppm, or about 1 ppm to about 9 ppm, or about 1 ppm to about 7 ppm, or about 1 ppm to about 6 ppm, or about 1 ppm to about 5 ppm, or about 3 ppm to about 6 ppm, or about 2 ppm to about 8 ppm. A low calcium second medium, according to some embodiments, may comprise a calcium concentration of at most about 10 ppm (e.g., ±1 ppm). In some embodiments, a low calcium second medium may comprise a calcium concentration of at most about 5 ppm (e.g., ±0.5 ppm). In some embodiments, soaking a biomass in a low calcium second medium may effect the equilibrium between an oxalic acid concentration and an oxalate concentration (e.g., calcium oxalate).

In some embodiments, a second medium may be configured to have a high calcium composition (e.g., a high calcium second medium). For example, a high calcium second medium may comprise a calcium concentration of ≤about 800 ppm, or ≤about 750 ppm, or ≤about 700 ppm, or ≤about 650 ppm, or ≤about 600 ppm, or ≤about 550 ppm, or ≤about 500 ppm, or ≤about 450 ppm, or ≤about 400 ppm, or ≤about 350 ppm, or ≤about 300 ppm, or ≤about 250 ppm, or ≤about 200 ppm, or ≤about 150 ppm, or ≤about 100 ppm, or ≤about 50 ppm. In some embodiments, a high calcium second medium may comprise a calcium concentration of about 50 ppm to about 200 ppm, or about 50 ppm to about 400 ppm, or about 50 ppm to about 600 ppm, or about 100 ppm to about 800 ppm, or about 100 ppm to about 700 ppm, or about 100 ppm to about 600 ppm, or about 100 ppm to about 500 ppm, or about 300 ppm to about 600 ppm, or about 200 ppm to about 800 ppm. A high calcium second medium, according to some embodiments, may comprise a calcium concentration of at most about 800 ppm (e.g., ±50 ppm). In some embodiments, a high calcium second medium may comprise a calcium concentration of at most about 600 ppm (e.g., ±50 ppm). In some embodiments, soaking a biomass in a high calcium second medium may effect the equilibrium between an oxalic acid concentration and an oxalate concentration (e.g., calcium oxalate). For example, soaking a biomass in a high calcium second medium may convert oxalic acid into oxalate.

In some embodiments, a second medium may be configured to have a low calcium composition and a low nitrogen composition (e.g., a low nitrogen and calcium growth medium). For example, a low nitrogen and calcium growth medium may comprise a calcium concentration of ≤about 20 ppm, or ≤about 18 ppm, or ≤about 16 ppm, or ≤about 14 ppm, or ≤about 12 ppm, or ≤about 10 ppm, or ≤about 9 ppm, or ≤about 8 ppm, or ≤about 7 ppm, or ≤about 6 ppm, or ≤about 5 ppm, or ≤about 4 ppm, or ≤about 3 ppm, or ≤about 2 ppm, or ≤about 1 ppm, or ≤about 0.5 ppm, or about 0 ppm. A low nitrogen and calcium growth medium may comprise a nitrogen concentration of ≤about 20 ppm, or ≤about 18 ppm, or ≤about 16 ppm, or ≤about 14 ppm, or ≤about 12 ppm, or ≤about 10 ppm, or ≤about 9 ppm, or ≤about 8 ppm, or ≤about 7 ppm, or ≤about 6 ppm, or ≤about 5 ppm, or ≤about 4 ppm, or ≤about 3 ppm, or ≤about 2 ppm, or ≤about 1 ppm, or ≤about 0.5 ppm, or about 0 ppm. In some embodiments, a low nitrogen and calcium second medium may comprise a calcium concentration of about 0 ppm to about 20 ppm, or about 0.5 ppm to about 20 ppm, or 0.5 ppm to about 15 ppm, or 0.5 ppm to about 10 ppm, or about 1 ppm to about 9 ppm, or about 1 ppm to about 7 ppm, or about 1 ppm to about 6 ppm, or about 1 ppm to about 5 ppm, or about 3 ppm to about 6 ppm, or about 2 ppm to about 8 ppm. In some embodiments, a low nitrogen and calcium second medium may comprise a nitrogen concentration of about 0 ppm to about 20 ppm, or about 0.5 ppm to about 20 ppm, or 0.5 ppm to about 15 ppm, or 0.5 ppm to about 10 ppm, or about 1 ppm to about 9 ppm, or about 1 ppm to about 7 ppm, or about 1 ppm to about 6 ppm, or about 1 ppm to about 5 ppm, or about 3 ppm to about 6 ppm, or about 2 ppm to about 8 ppm. A low nitrogen and calcium second medium, according to some embodiments, may comprise a calcium concentration of at most about 10 ppm (e.g., ±1 ppm). In some embodiments, a low nitrogen and calcium second medium may comprise a calcium concentration of at most about 5 ppm (e.g., ±0.5 ppm). A low nitrogen and calcium second medium, according to some embodiments, may comprise a nitrogen concentration of at most about 10 ppm (e.g., ±1 ppm). In some embodiments, a low nitrogen and calcium second medium may comprise a nitrogen concentration of at most about 5 ppm (e.g., ±0.5 ppm). In some embodiments, soaking a biomass in a low nitrogen and low calcium second medium may effect the equilibrium between an oxalic acid concentration and an oxalate concentration (e.g., calcium oxalate).

Soaking a biomass may comprise submerging a biomass in a second medium to form a biomass slurry, according to some embodiments. In some embodiments, a biomass may be soaked for about 1 hour, or about 2 hours, or about 4 hours, or about 6 hours, or about 8 hours, or about 10 hours, or about 12 hours, or about 16 hours, or about 20 hours, or about 24 hours, or about 36 hours, or about 48 hours, or about 60 hours, or about 72 hours, or about 84 hours, or about 96 hours, or about 108 hours, or about 120 hours, or about 132 hours, or about 144 hours. Soaking a biomass may include agitation, flow, movement, spraying, or stirring of a second medium. According to some embodiments, a biomass slurry, including a soaked microcrop (e.g., *Lemna*) and a second medium (e.g., a low nitrogen second medium), may be conveyed to an inclined vibrating screen where a biomass (e.g., microcrop) may be separated from the second medium.

According to some embodiments a biomass may be buffered in a third medium, according to some embodiments (e.g., 110). A third medium may comprise water (e.g., ground water, surface water, recycled water), distilled water, reverse osmosis water and/or nanofiltered water, according to some embodiments. In some embodiments, a third medium may comprise any desired portion of recycled fluid. For example, a third medium may comprise at least about 10% (v/v), at least about 20% (v/v), at least about 30% (v/v), at least about 40% (v/v), at least about 50% (v/v), at least about 60% (v/v), at least about 70% (v/v), at least about 80% (v/v), or at least about 90% (v/v) recycled fluid from another stage of the process (e.g., a reject stream from filtration 260, 254).

Buffering a biomass (e.g., 110 of FIG. 1C) may comprise submerging a biomass in a third medium to form a biomass slurry, according to some embodiments. In some embodiments, a biomass may be buffered for about 1 hour, or about 2 hours, or about 4 hours, or about 6 hours, or about 8 hours, or about 10 hours, or about 12 hours, or about 16 hours, or about 20 hours, or about 24 hours, or about 36 hours, or about 48 hours. According to some embodiments, a biomass slurry, including a buffered microcrop (e.g., *Lemna*) and a third medium (e.g., distilled water, ground water, surface water, rain water), may be conveyed to an inclined vibrating screen where a biomass (e.g., microcrop) may be separated from the third medium. In other embodiments, a biomass (e.g., microcrop) may be separated from the third medium by draining.

According to some embodiments, buffering a biomass may include changing (e.g., raise, lower) or maintaining a pH value of the biomass. In some embodiments, buffering a biomass may comprise changing (e.g., raising, lowering) or maintaining a pH value of a biomass to below about 8.0, or below about 7.5, or below about 7.0, or below about 6.5, or below about 6.0, or below about 5.5, or below about 5.0, or below about 4.5, or below about 4.0, or below about 3.5, or below about 3.0. According to some embodiments, buffering a biomass may comprise changing (e.g., raising, lowering) or maintaining a pH value of a biomass to a range of: from about 3.0 to about 7.5, or from about 3.5 to about 7.5, or from about 4.0 to about 7.5, or from about 4.5 to about 7.5, or from about 5.0 to about 7.5, or from about 5.5 to about 7.5, or from about 6.0 to about 7.5, or from about 6.5 to about 7.5. As would be appreciated by someone having ordinary skill in the art, buffering a biomass by adjusting a pH value of a biomass may promote protein stability which may, in some embodiments, promote greater protein yields in comparison to a non-buffered biomass.

One or more of a soaked biomass and a buffered biomass generated in one procedure may be stored in their respective container (e.g., soaking container, buffering container) before being fed to one or more downstream procedures or apparatuses. This may accommodate different operation schedules or modes including, for example, continuous mode, batch mode, or multiple feeding streams to one or more downstream procedure(s) and/or apparatus(es). For example, in some embodiments, a biomass may be harvested during daylight hours and processed (e.g., soaking and/or buffering), subsequently the processed biomass may be further processed (e.g., lysing, separating) in smaller batches (e.g., a first portion, a second portion) to accommodate the capacity limitations of the downstream processing machinery.

Washing a Biomass

In some embodiments, processing a microcrop or biomass (e.g., first portion, second portion) may include a wash procedure to remove excess growth medium, debris, contaminants, microorganisms, and/or toxins. A wash procedure may be performed on a biomass: (1) after harvesting (e.g., 104); or (2) after harvesting and soaking (e.g., 108); or (3) after harvesting and buffering (e.g., 110); or (4) or after harvesting, soaking, and buffering. Washing a biomass may increase protein purity and/or yield. A wash procedure may disinfect and/or disinfest a biomass, reducing or removing bacteria, fungi, viruses, insects, and any combination thereof which are on or around the surfaces of the biomass. In some embodiments a wash procedure may be performed by exposing (e.g., submerging, spraying) at least one surface of a biomass to a wash solution (e.g., water, growth medium, antimicrobial solution). A wash solution, in some embodiments, may be combined with a biomass (e.g., first portion, second portion) to form a slurry.

In some embodiments, a wash solution may comprise any desired portion of recycled fluid. For example, a wash solution may comprise at least about 10% (v/v), at least about 20% (v/v), at least about 30% (v/v), at least about 40% (v/v), at least about 50% (v/v), at least about 60% (v/v), at least about 70% (v/v), at least about 80% (v/v), or at least about 90% (v/v) recycled fluid from another stage of the process (e.g., recycled wash solution 106, a reject stream from filtration 260, 254). In some embodiments a wash solution may be an aqueous solution or solvent. A wash solution may contain one or more antimicrobials, de-infestation compounds, fatty acids, alcohols, chlorine, oxidizing compounds, and any combination thereof (e.g., ozonated water).

According to some embodiments a wash solution may be applied at an elevated temperature and/or high pressure. A wash solution may remain in contact with a biomass for at least about 1 second, or for at least about 5 seconds, or for at least about 10 seconds, or for at least about 20 seconds, or for at least about 30 seconds, or for at least about 1 minute, or for at least about 5 minutes. In some embodiments, a second wash solution (e.g., water, ozonated water, a recycled wash solution (e.g., 106) may be applied to a biomass. A third wash solution (e.g., water, ozonated water, recycled wash solution) may be applied to a biomass, in some embodiments. A composition of a first wash solution, a second wash solution, and a third wash solution may be the same or different from one another. In some embodiments a first wash solution may be or may comprise a reject stream from a filtration process (e.g., 254, 260), a second wash solution may be water, and a third wash solution may be ozonated water. Some or all of a wash solution (e.g., a first, second, and/or third wash solution), in some embodiments, may be separated from a biomass (e.g., using an inclined screen or vibratory screen).

In some embodiments, some or all of a wash solution, second wash solution, and/or third wash solution may be collected and reused/recycled (e.g., 106). At least about 40%, or at least about 50%, or at least about 60%, or at least about 70%, or at least about 80%, or at least about 90%, or at least about 95% of a wash solution, second wash solution, and/or third wash solution (e.g., water) separated from the biomass may be recycled for future use (e.g., recycled wash solution 106; used as growth medium in the bioreactor system 102), according to some embodiments.

A wash solution (e.g., a first, second, and/or third wash solution) may have a temperature below room temperature (e.g., about 12° C.) at the time of use. Cooling a wash solution, and thereby the microcrop, may improve protein recovery efficiency and/or decrease proteolytic activity. In some embodiments, a wash solution (e.g., a first, second, and/or third wash solution) may have a temperature below about 30° C., or below about 20° C., or below about 15° C., or below about 10° C., or below about 5° C., or below about 2° C., or below about 1° C., or below about 0° C. at the time of use. A wash solution (e.g., a first, second, and/or third wash solution) may have a temperature between about 0° C. and about 10° C., or between about 5° C. and about 15° C., or between about 10° C. and about 20° C., or 15° C. and about 25° C., or between about 20° C. and about 30° C. at the time of use, in some embodiments.

In some embodiments, a wash solution (e.g., a first, second, and/or third wash solution) may have a temperature above room temperature (e.g., about 50° C.) at the time of use. Heating a wash solution, and thereby the microcrop, may improve protein recovery efficiency, decrease proteolytic activity (e.g., denature proteolytic enzymes), and/or decrease microbial contamination (e.g., pasteurization). In some embodiments, a wash solution (e.g., a first, second, and/or third wash solution) may have a temperature above about 20° C., or above about 25° C., or above about 30° C., or above about 35° C., or above about 40° C., or above about 45° C., or above about 50° C., or above about 55° C., or above about 60° C., or above about 65° C., or above about 70° C., or above about 75° C., or above about 80° C., or above about 85° C., or above about 90° C., or above about 95° C., or above about 100° C. at the time of use. A wash solution (e.g., a first, second, and/or third wash solution) may have a temperature between about 40° C. and about 50° C., or between about 45° C. and about 55° C., or between about 50° C. and about 60° C. at the time of use, in some embodiments. According to some embodiments, a wash solution (e.g., a first, second, and/or third wash solution) may have a temperature between about 75° C. and about 80° C., or between about 80° C. and about 85° C., or between about 85° C. and about 90° C., or between about 90° C. and about 95° C., or between about 95° C. and about 100° C. at the time of use. In some embodiments, a wash solution (e.g., a first, second, and/or third wash solution) may have a temperature between about 50° C. and about 80° C., or between about 55° C. and about 85° C., or between about 60° C. and about 90° C., or between about 65° C. and about 95° C., or between about 70° C. and about 100° C. at the time of use.

Lysing a Biomass

According to some embodiments a biomass may be lysed to form a lysed biomass (e.g., first portion, second portion). Lysing may be performed on a biomass: (1) after harvesting (e.g., 104); or (2) after harvesting and soaking (e.g., 108); or (3) after harvesting and buffering (e.g., 110); or (4) or after harvesting, soaking, and buffering; or (5) after harvesting and washing; or (6) after harvesting, soaking, and washing; or (7) after harvesting, buffering, and washing; or (8) after harvesting, soaking, buffering, and washing.

As used herein, lysing may include mechanical, chemical, and/or ultrasonic (e.g., sonication) procedures that disturb the organization of the organism on the level of individual cells or multicellular structures. Lysing may include, in some embodiments, rendering carbohydrates, proteins, and micronutrients present in a microcrop more available for downstream processing to purified protein, carbohydrate-containing materials, and/or micronutrient-containing fluids. According to some embodiments, lysing may be achieved using a combination of mechanical, chemical, and/or ultrasonic (e.g., sonication) methods.

In some embodiments, lysing may be performed at temperatures below room temperature. Lysing a microcrop at a lower temperature may improve yields, for example, by limiting or decreasing undesired enzymatic activity (e.g., proteolytic activity). Lysing may be performed, in some embodiments, at a temperature below about 30° C., or below about 20° C., or below about 15° C., or below about 10° C., or below about 15° C., or below about 10° C., or below about 5° C., or below about 2° C., or below about 1° C., or below about 0° C. A lysing fluid (e.g., water, recycled water, reverse osmosis water) may be added to a biomass, washed or unwashed, before or during lysing according to some embodiments. For example, at least about 10%, at least about 20%, at least about 30%, at least about 40%, at least about 50%, at least about 60%, at least about 70%, at least about 80%, or at least about 90% of lysing fluid may be water generated as the result of reverse osmosis/nanofiltration of a filtration product (e.g., 260). In some embodiments a lysing fluid may be at a temperature below about 30° C., or below about 20° C., or below about 15° C., or below about 10° C., or below about 5° C., or below about 2° C., or below about 1° C., or below about 0° C. A lysing fluid, in some embodiments, may include buffers, protease inhibitors, anti-microbial agents, chelators (e.g., EDTA), reducing agents, or any combination thereof.

According to some embodiments, lysing may be performed at temperatures above room temperature (e.g., about 40° C.), for example, to enhance cellulosic breakdown and/or denature undesired enzymes (e.g., proteolytic enzymes). Lysing may be performed at a temperature above about 30° C., or above about 35° C., or above about 37° C., or above about 40° C., in some embodiments.

Lysing may include, for example, chopping, shredding, smashing, pressing, tearing, ultrasonic treatment (e.g., sonication), lysis by osmotic pressure, chemical treatments that degrade biological structures, or any combination thereof. In some embodiments, lysing is achieved in a mechanical way (also referred to as milling), for example, by milling, grinding, or shredding the biomass to generate a lysed biomass. A lysing process may be achieved using, for example, a shear mill, a ball mill, a colloid mill, a knife mill, a hammer mill, a grinding mill, a puree machine, a filter press, a mechanical press or any combination thereof.

In some embodiments, entry into or exit from a lysing (e.g., milling) process may be metered at any desired volume, mass, or other rate or interval (e.g., a constant rate, a variable rate, continuously, semi-continuously, periodically, intermittently). A feed rate and/or mode may be determined based on considerations including, for example: the target production rate; apparatus(es) employed in a process; properties of a feedstock, or any combination thereof. A feed rate, in some embodiments, is at least about 10 kg/hour, or at least about 50 kg/hour, or at least about 100 kg/hour, or at least about 200 kg/hour, or at least about 300 kg/hour, or at least about 400 kg/hour, or at least about 500 kg/hour, or at least about 600 kg/hour, or at least about 700 kg/hour, or at least about 800 kg/hour, or at least about 900 kg/hour, or at least about 1000 kg/hour, or at least about 1200 kg/hour, or at least about 1400 kg/hour, or at least about 1600 kg/hour, or at least about 1800 kg/hour, or at least about 2000 kg/hour, or at least about 2200 kg/hour. In some embodiments, the feeding rate is from about 10 kg/hour to about 200 kg/hour, or from about 200 kg/hour to about 400 kg/hour, or from about 400 kg/hour to about 600 kg/hour, or from about 600 kg/hour to about 800 kg/hour, or from about 800 kg/hour to about 1000 kg/hour, or from about 1000 kg/hour to about 1200 kg/hour, or from about 1200 kg/hour to about 1400 kg/hour, or from about 1400 kg/hour to about 1600 kg/hour, or from about 1600 kg/hour to about 1800 kg/hour, or from about 1800 kg/hour to about 2000 kg/hour, or from about 2000 kg/hour to about 2200 kg/hour.

Chemical methods may be employed, in some embodiments, (e.g., alone or in combination with mechanical methods) to lyse a biomass or washed biomass. Enzymes (e.g., cellulase) may be used, in some embodiments to breakdown or assist in breakdown of cellular structures. In some embodiments lysing may be performed, for example, by changing the pH value of a biomass (e.g., harvested microcrop). The pH value, in some embodiments, may be raised to higher than about 7.0, or higher than about 7.5, or higher than about 8.0, or higher than about 8.5, or higher than about 9.0, or higher than about 9.5, or higher than about 10.0. According to some embodiments, the pH value of a biomass may be maintained from about 7.0 to about 7.5, or from about 7.5 to about 8.0, or from about 8.0 to about 8.5, or from about 8.5 to about 9.0, or from about 9.0 to about 9.5, or from about 9.5 to about 10.0. The pH value of a biomass may be maintained from about 7.0 to about 14.0, or from about 7.0 to about 13.0, or from about 7.0 to about 12.0, or from about 7.0 to about 11.0, or from about 7.0 to about 10.0, or from about 7.0 to about 10.5, or from about 7.0 to about 10.0, or from about 7.0 to about 9.5, or from about 7.0 to about 9.0, or from about 7.0 to about 8.5, or from about 7.0 to about 8.0, or from about 7.0 to about 7.5, in some embodiments. In some embodiments the pH value may be lowered to below about 7.0, or below about 6.5, or below about 6.0, or below about 5.5, or below about 5.0, or below about 4.5, or below about 4.0, or below about 3.5, or below about 3.0. The pH value of a biomass, in some embodiments, may be maintained from about 3.0 to about 3.5, or from about 3.5 to about 4.0, or from about 4.0 to about 4.5, or from about 4.5 to about 5.0, or from about 5.0 to about 5.5, or from about 5.5 to about 6.0, or from about 6.0 to about 6.5, or from about 6.5 to about 7.0. The pH value of a biomass may be maintained from about 3.0 to about 7.0, or from about 3.5 to about 7.0, or from about 4.0 to about 7.0, or from about 4.5 to about 7.0, or from about 5.0 to about 7.0, or about 50 from about 5.5 to about 7.0, or from about 6.0 to about 7.0, or from about 6.5 to about 7.0, according to some embodiments.

In some embodiments, a lysed biomass (e.g., a mechanically lysed biomass) may pass to the next step or procedure for isolating protein and/or other product(s) with or without neutralization. For example, a lysed biomass may be fed directly to the next procedure or it may be first pH-adjusted (e.g., neutralized, acidified, basified). Precipitating agents (e.g., salts) may be added, in some embodiments, to a lysed microcrop to precipitate dissolved compounds.

A lysed biomass (e.g., first portion, second portion) may be at a temperature below room temperature (e.g., about 12° C.), in some embodiments. Cooling a lysed biomass may improve protein recovery efficiency and/or decrease proteolytic activity. A lysed biomass, in some embodiments, may have a temperature below about 30° C., or below about 20° C., or below about 15° C., or below about 10° C., or below about 15° C., or below about 10° C., or below about 5° C., or below about 2° C., or below about 1° C., or below about 0° C. at the time of use. According to some embodiments, a lysed biomass may have a temperature between about 0° C. and about 10° C., or between about 5° C. and about 15° C., or between about 10° C. and about 20° C., or between about 15° C. and about 25° C., or between about 20° C. and about 30° C. at the time of use.

In some embodiments, a lysed biomass (e.g., first portion, second portion) may have a temperature above room temperature (e.g., about 50° C.) at the time of use. Heating a lysed biomass may improve protein recovery efficiency, decrease proteolytic activity (e.g., denature proteolytic enzymes), and/or decrease microbial contamination (e.g., pasteurization). In some embodiments, a lysed biomass may have a temperature above about 20° C., or above about 25° C., or above about 30° C., or above about 35° C., or above about 40° C., or above about 45° C., or above about 50° C., or above about 55° C., or above about 60° C., or above about 65° C., or above about 70° C., or above about 75° C., or above about 80° C., or above about 85° C., or above about 90° C. at the time of use. A lysed biomass may have a temperature between about 40° C. and about 50° C., or between about 45° C. and about 55° C., or between about 50° C. and about 60° C. at the time of use, in some embodiments. According to some embodiments, a lysed biomass may have a temperature between about 75° C. and about 80° C., or between about 80° C. and about 85° C. at the time of use.

Precipitating Oxalate from a Lysed Biomass

According to some embodiments, at least some soluble oxalic acid may be removed from a lysed biomass by converting the oxalic acid to an oxalate (e.g., calcium oxalate) and precipitating (e.g., 123) the oxalate from the lysed biomass (e.g., 122, 222). In some embodiments, precipitating an oxalate from a lysed biomass may include mixing at least a portion of the lysed biomass with at least one calcium salt (e.g., calcium chloride, calcium acetate). Precipitating an oxalate from a lysed biomass, in some embodiments, may include mixing at least a portion of the lysed biomass with a calcium carbonate or calcium hydroxide solution. Precipitated oxalate may be removed from the biomass by centrifugation and/or filtration, according to some embodiments.

Separating a Biomass

A biomass (e.g., Lemna) may be separated (e.g., 124, 224) to generate a juice fraction (e.g., 226) and a solid fraction (e.g., 228). A juice fraction (e.g., first portion, second portion) may include a protein-rich liquid and/or at least about some solid particles (e.g., carbohydrates, fiber). In some embodiments a biomass (e.g., washed, lysed) may be diluted with a dilution fluid (e.g., water, recycled water, reverse osmosis water) prior to separation.

A dilution fluid may be at a temperature below room temperature (e.g., about 12° C.), in some embodiments. Cooling a dilution fluid may improve protein recovery efficiency and/or decrease proteolytic activity. A dilution fluid, in some embodiments, may have a temperature below about 30° C., or below about 20° C., or below about 15° C., or below about 10° C., or below about 15° C., or below about 10° C., or below about 5° C., or below about 2° C., or below about 1° C., or below about 0° C. at the time of use. According to some embodiments, a dilution fluid may have a temperature between about 0° C. and about 10° C., or between about 5° C. and about 15° C., or between about 10° C. and about 20° C., or between about 15° C. and about 25° C., or between about 20° C. and about 30° C. at the time of use.

In some embodiments, a dilution fluid may have a temperature above room temperature (e.g., about 50° C.) at the time of use. Heating a dilution fluid may improve protein recovery efficiency, decrease proteolytic activity (e.g., denature proteolytic enzymes), and/or decrease microbial contamination (e.g., pasteurization). In some embodiments, a dilution fluid may have a temperature above about 20° C., or above about 25° C., or above about 30° C., or above about 35° C., or above about 40° C., or above about 45° C., or above about 50° C., or above about 55° C., or above about 60° C., or above about 65° C., or above about 70° C., or above about 75° C., or above about 80° C., or above about 85° C., or above about 90° C. at the time of use. A dilution fluid may have a temperature between about 40° C. and about 50° C., or between about 45° C. and about 55° C., or between about 50° C. and about 60° C. at the time of use, in some embodiments. According to some embodiments, a dilution fluid may have a temperature between about 75° C. and about 80° C., or between about 80° C. and about 85° C. at the time of use.

A dilution fluid, in some embodiments, may include buffers, protease inhibitors, anti-microbial agents, chelators (e.g., EDTA), reducing agents, or any combination thereof.

In some embodiments a lysed biomass or diluted lysed biomass may be sonicated prior to separation. Sonication may increase protein yield.

Separating a biomass to form a juice fraction and a solid fraction may involve pressing (e.g., belt press, filter press), centrifugation, filtration, pressurized filtration, or any combination thereof. Interchangeable unit operations for separating a biomass include, for example, a decanter centrifuge, a belt press, a fan press, a rotary press, a screw press, a filter press, a finisher press, or any combination thereof.

In some embodiments, a biomass may be metered to a separating mechanism at any desired volume, mass, or other rate or interval (e.g., a constant rate, a variable rate, continuously, semi-continuously, periodically, intermittently). A feed rate and/or mode may be determined based on considerations including, for example: the target production rate; apparatus(es) employed in the process; properties of the feedstock; or any combination thereof. A feeding rate, in some embodiments, may be at least about 10 kg/hour, or at least about 50 kg/hour, or at least about 100 kg/hour, or at least about 200 kg/hour, or at least about 300 kg/hour, or at least about 400 kg/hour, or at least about 500 kg/hour, or at least about 600 kg/hour, or at least about 700 kg/hour, or at least about 800 kg/hour, or at least about 900 kg/hour, or at least about 1000 kg/hour, or higher than about 1000 kg/hour. According to some embodiments, the feeding rate may be from about 10 kg/hour to about 200 kg/hour, or from about 200 kg/hour to about 400 kg/hour, or from about 400 kg/hour to about 600 kg/hour, or from about 600 kg/hour to about 800 kg/hour, or from about 800 kg/hour to about 1000 kg/hour, or from about 1000 kg/hour to about 1200 kg/hour, or from about 1200 kg/hour to about 1400 kg/hour, or from about 1400 kg/hour to about 1600 kg/hour, or from about 1600 kg/hour to about 1800 kg/hour, or from about 1800 kg/hour to about 2000 kg/hour, or from about 2000 kg/hour to about 2200 kg/hour.

Separating a biomass may be performed at any desired temperature. Separating may be performed at temperatures below room temperature, for example, to decrease proteolytic activity. In some embodiments, separating may be performed at a temperature below about 40° C., below about 30° C., or below about 20° C., or below about 15° C., or below about 10° C., or below about 15° C., or below about 10° C., or below about 5° C., or below about 2° C., or below about 1° C., or below about 0° C. Separating may be performed, for example, at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C.

Precipitating Oxalate from a Juice Fraction

According to some embodiments, at least some soluble oxalic acid may be removed from a juice fraction by conversion to oxalate and precipitation. In some embodiments, precipitating a juice fraction may include mixing at least a portion of the juice fraction with at least one calcium salt (e.g., calcium chloride, calcium acetate). Precipitating a juice fraction, in some embodiments, may include mixing at least a portion of the juice fraction with a calcium carbonate solution or a calcium hydroxide solution. Precipitated oxalate may be removed from the biomass by centrifugation and/or filtration, according to some embodiments.

Separating a Juice Fraction

A juice fraction (e.g., first portion, second portion) may be separated to generate a first juice and a first cake, according to some embodiments. A first juice (e.g., first portion, second portion) may include a dissolved protein. In some embodiments, buffers, protease inhibitors, anti-microbial agents, chelators (e.g., EDTA), reducing agents, or any combination thereof may be added to a juice fraction and/or a first juice. Separating a juice fraction, in some embodiments, may include centrifugation, filtration, pressurized filtration, or any combination thereof. Two or more unit operations (e.g., interchangeable unit operations) may be used to separate a juice fraction including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof.

Microfiltration may be used, in some embodiments, to separate a juice fraction into a first juice and a first cake. In some embodiments, suitable filter sizes may include ≤about 10 µm, or ≤about 5 µm, or ≤about 3 µm, or ≤about 2 µm, or ≤about 1 µm, or ≤about 0.5 µm, or ≤about 0.4 µm, or ≤about 0.3 µm, or ≤about 0.2 µm, or ≤about 0.1 µm. A filter may have a filter size of not less than about 0.1 µm, in some embodiments. Microfiltration may reduce the concentration of suspended solids (e.g., fats, fiber), microbial contamination (e.g., *Escherichia coli*), and/or fungal contamination (e.g., yeast) in the first juice, according to some embodiments.

In some embodiments, a vacuum may be implemented during at least some of separating process.

Separating may be performed, according to some embodiments, at temperatures below room temperature, for example, to decrease proteolytic activity. In some embodiments separating may be performed at a temperature below about 40° C., or below about 30° C., or below about 20° C., or below about 15° C., or below about 10° C., or below about 5° C., or below about 2° C., or below about 1° C., or below about 0° C. Separating may be performed at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C., in some embodiments.

A first juice may be pumped into a storage tank, for example, a chilled storage tank, until further processing. In some embodiments a chilled storage tank may be maintained at a temperature below room temperature (e.g., 12° C.). Storage of a first juice at a low temperate may reduce proteolytic activity and thereby improve protein recovery efficiency. A chilled storage tank, in some embodiments, may be maintained at a temperature below about 30° C., or below about 20° C., or below about 15° C., or below about 10° C., or below about 5° C., or below about 2° C., or below about 1° C., or below about 0° C. According to some embodiments, a chilled storage tank may be maintained at a temperature of about 5° C., about 6° C., about 7° C., about 8° C., about 9° C., about 10° C., about 11° C., about 12° C., about 13° C., about 14° C., or about 15° C. In some embodiments, a first juice may be fed directly to further processing without being stored in a storage tank.

Any one or more of the liquid phases (e.g., a juice fraction, a first juice, a second juice, a third juice) or solid phases (e.g., a solid fraction, a first cake, a second cake) generated in one procedure may be stored in the storage tank before being fed to one or more downstream procedures or apparatuses. In some embodiments a homogeneous liquid phase or solid phase may be generated for the downstream procedure(s) or apparatus(es). This may accommodate different operation schedules or modes including, for example, continuous mode, batch mode, or multiple feeding streams to one or more downstream procedure(s) and/or apparatus (es). A liquid phase or solid phase may be maintained in a storage tank at a desirable temperature (e.g., below room temperature, such as 12° C.) to reduce degradation and maintain high quality until further processing.

Separating a Solid Fraction

In some embodiments, a solid fraction may be further separated to extract additional juice (e.g., a second juice 232). Separation of a solid fraction (e.g., first portion, second portion) may form a second juice (e.g., 232) and a first solid (e.g., 234). A second juice (e.g., first portion, second portion) may include a protein-rich liquid and/or at least some solid particles (e.g., carbohydrates, fiber).

Separating a solid fraction to form a second juice and a first solid may involve pressing (e.g., screw press), centrifugation, filtration, pressurized filtration, or any combination thereof. Interchangeable unit operations for separating a solid fraction include, for example, a decanter centrifuge, a belt press, a fan press, a rotary press, a screw press, a filter press, a finisher press, or any combination thereof.

In some embodiments, a solid fraction may be metered to a separating mechanism at any desired volume, mass, or other rate or interval (e.g., a constant rate, a variable rate, continuously, semi-continuously, periodically, intermittently). A feed rate and/or mode may be determined based on considerations including, for example: the target production rate; apparatus(es) employed in the process; properties of the feedstock; or any combination thereof. A feeding rate, in some embodiments, may be at least about 10 kg/hour, or at least about 50 kg/hour, or at least about 100 kg/hour, or at least about 200 kg/hour, or at least about 300 kg/hour, or at least about 400 kg/hour, or at least about 500 kg/hour, or at least about 600 kg/hour, or at least about 700 kg/hour, or at least about 800 kg/hour, or at least about 900 kg/hour, or at least about 1000 kg/hour, or higher than about 1000 kg/hour. According to some embodiments, the feeding rate may be from about 10 kg/hour to about 200 kg/hour, or from about 200 kg/hour to about 400 kg/hour, or from about 400 kg/hour to about 600 kg/hour, or from about 600 kg/hour to about 800 kg/hour, or from about 800 kg/hour to about 1000 kg/hour, or higher than about 1000 kg/hour, or from about 1000 kg/hour to about 1200 kg/hour, or from about 1200 kg/hour to about 1400 kg/hour, or from about 1400 kg/hour to about 1600 kg/hour, or from about 1600 kg/hour to about 1800 kg/hour, or from about 1800 kg/hour to about 2000 kg/hour, or from about 2000 kg/hour to about 2200 kg/hour.

Separating a solid fraction may be performed at any desired temperature. Separating may be performed at temperatures below room temperature, for example, to decrease proteolytic activity and/or microbial growth. In some embodiments, separating may be performed at a temperature below about 40° C., below about 30° C., or below about 20° C., or below about 15° C., or below about 10° C., or below about 5° C., or below about 2° C., or below about 1° C., or below about 0° C. Separating may be performed, for example, at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C.

In some embodiments, a separation apparatus (e.g., screw press) selected to separate a solid fraction may be the same apparatus used to separate a biomass (e.g., lysed) to form a juice fraction and a solid fraction. A separation apparatus (e.g., screw press) selected to separate a solid fraction may be a different apparatus than that used to separate (e.g., decanter centrifuge) a biomass (e.g., lysed) to form a juice fraction and a solid fraction, in some embodiments. In some embodiments, a separation apparatus (e.g., screw press) may be used multiple times to extract additional second juice from a solid fraction.

Figure 2A:
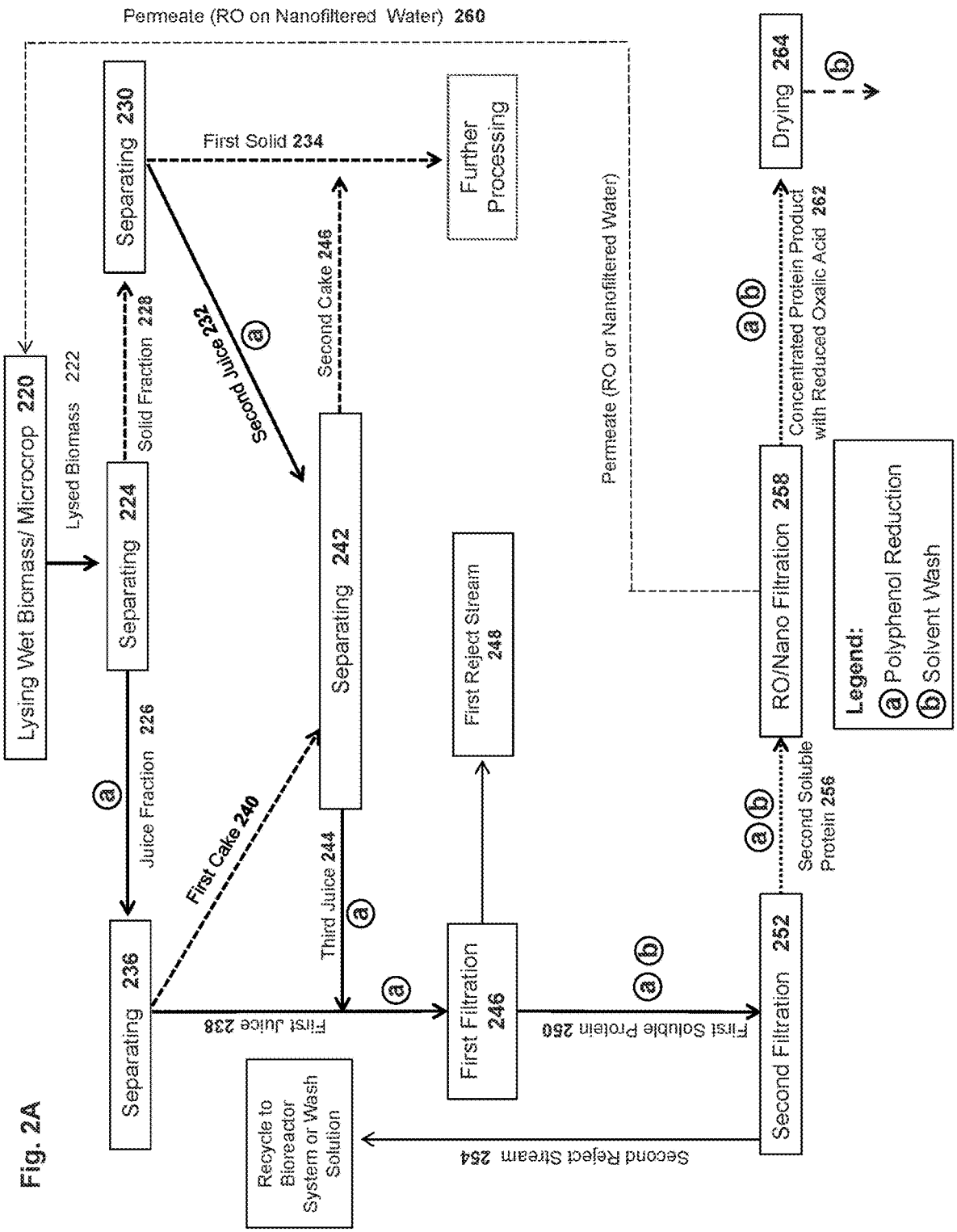
FIG. 2A is a flow diagram illustrating a process for producing a protein concentrate having a reduced oxalic acid content from a biomass according to a specific example embodiment of the disclosure.
Figure 2B:
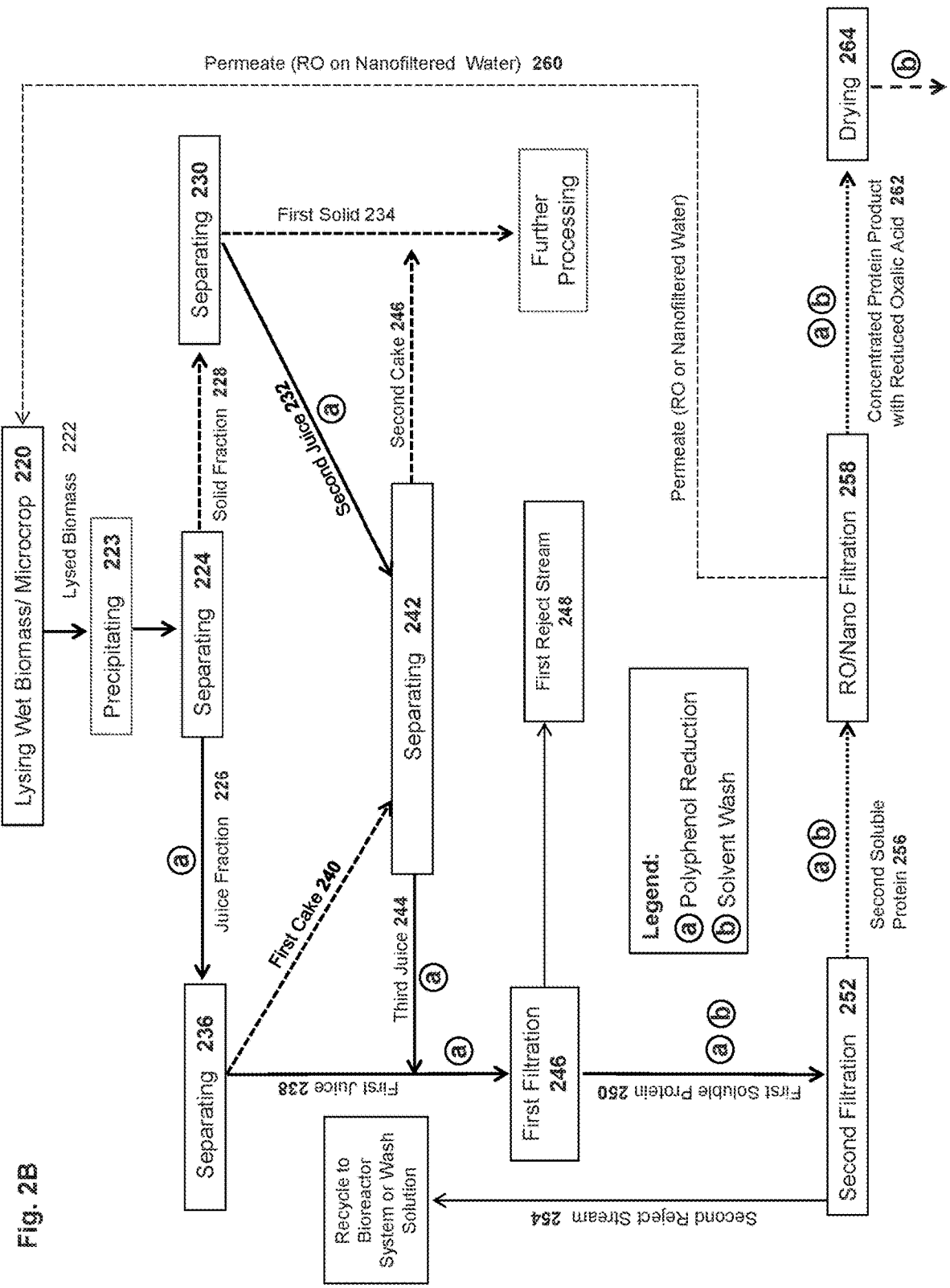
FIG. 2B is a flow diagram illustrating a process for producing a protein concentrate having a reduced oxalic acid content from a biomass according to a specific example embodiment of the disclosure.
Figure 2C:
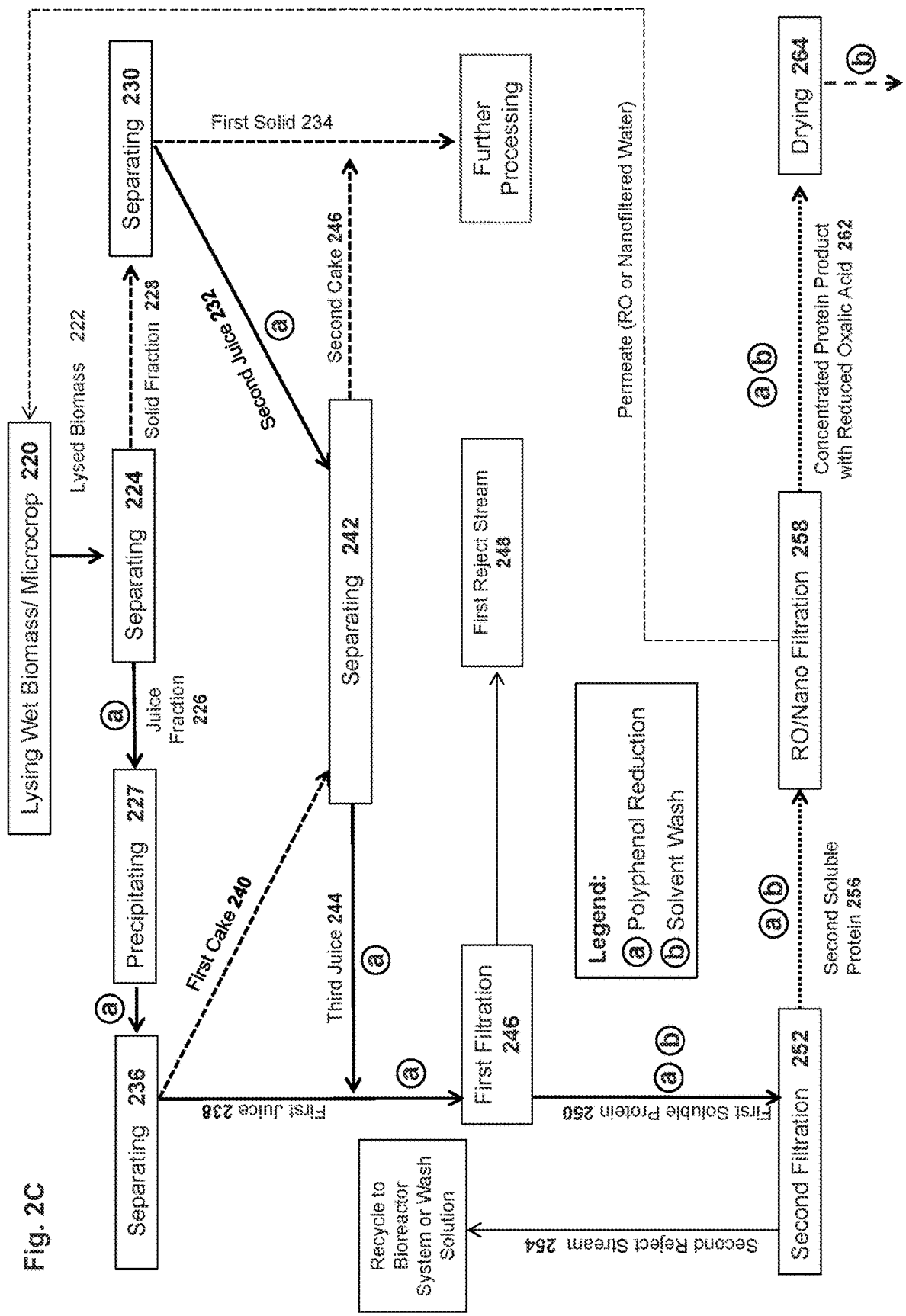
FIG. 2C is a flow diagram illustrating a process for producing a protein concentrate having a reduced oxalic acid content from a biomass according to a specific example embodiment of the disclosure.

According to some embodiments, a process for growing, harvesting, and separating a microcrop (e.g., aquatic plant species, *Lemna*, algal species) may be single cycle and at least one of a first cake (e.g., 240) and a second cake (e.g., 246) which are collected at other stages in the cycle (e.g., separation of a juice fraction yields a first cake) may be combined with a first solid to form a solid mixture, and the solid mixture may be further processed (e.g., FIGS. 2A, 2B, 2C).

In some embodiments a process for growing, harvesting, and separating a microcrop (e.g., aquatic plant species, *Lemna*, algal species) may be multiple cycles or a continuous process such that one or more of a first cake and a second cake that are collected in an earlier cycle may be combined with a solid fraction from a subsequent cycle prior to separation of the solid fraction.

Increasing the extraction of a second juice from a solid fraction may decrease the overall moisture content of a first solid and may thereby lower the energy expenditure required to further process the first solid (e.g., energy required to dry). Additionally, increasing the extraction of juice from a solid fraction and/or solid mixture may improve the yield of a protein-rich product.

In some embodiments, a moisture content of a solid fraction and/or solid mixture is less than about 90%, or less than about 80%, or less than about 70%, or less than about 60%, or less than about 50%, or less than about 40%, or less than about 30%, or less than about 20%, or less than about 10% by weight.

Separating a First Cake and/or a Second Juice

In some embodiments, further processing of a first cake (e.g., first portion, second portion) (e.g., 240) and a second juice (e.g., first portion, second portion) (e.g., 232) may be performed. Such additional processing may increase product yield and/or quality. In some embodiments, a first cake and a second juice may be combined and further separated (e.g., 242) to form a third juice and a second cake. A first cake and a second juice may be independently subjected to further separation, according to some embodiments.

Separating (e.g., 242) a first cake, a second juice, or any combination thereof may involve vibratory separation, centrifugation, filtration, pressurized filtration, or any combination thereof. Several different interchangeable unit operations may be used to separate including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof.

In some embodiments, filtration (e.g., a vibratory separator) may be used to separate a first cake, a second juice, or any combination thereof to form a third juice and a second cake. Suitable filter sizes may include, in some embodiments, a pore size of ≤about 800 µm, or ≤about 600 µm, or ≤about 500 µm, or ≤about 400 µm, or ≤about 300 µm, or ≤about 200 µm, or ≤about 180 µm, or ≤about 150 µm, or ≤about 120 µm, or ≤about 100 µm, or ≤about 90 µm, or ≤about 80 µm, or ≤about 70 µm, or ≤about 60 µm, or ≤about 50 µm, or ≤about 40 µm, or ≤about 30 µm, or ≤about 25 µm, or ≤about 20 µm, or ≤about 15 µm, or ≤about 10 µm, or ≤about 5 µm, or ≤about 1 µm. A filter may have a filter size of not more than about 800 µm, in some embodiments. Pore size of a filter may be selected larger or smaller as desired. For example, a larger pore size may be desirable where removal of contaminant material is of interest. A smaller pore size may be desirable where limiting the number of cycles of the process and/or protein yield is of interest. In some embodiments, a pore size of a filter may be selected based on lysing conditions, for example, an average particle size of a lysed biomass. A pore size of a filter may be selected based on one or more characteristics of a microcrop (e.g., cell wall composition, protein composition), according to some embodiments.

Microfiltration may be used, in some embodiments, to separate a first cake, a second juice, or any combination thereof to form a third juice and a second cake. In some embodiments, suitable filter sizes may include ≤about 10 µm, or ≤about 5 µm, or ≤about 3 µm, or ≤about 2 µm, or ≤about 1 µm, or ≤about 0.5 µm, or ≤about 0.4 µm, or ≤about 0.3 µm, or ≤about 0.2 µm, or ≤about 0.1 µm. A microfilter may have a filter size of not less than about 0.1 µm, in some embodiments.

In some embodiments, a vacuum may be implemented during at least some of separating process.

Separating (e.g., 242) may be performed, according to some embodiments, at temperatures below room temperature, for example, to decrease proteolytic activity. In some embodiments separating may be performed at a temperature below about 40° C., or below about 30° C., or below about 20° C., or below about 15° C., or below about 10° C., or below about 15° C., or below about 10° C., or below about 5° C., or below about 2° C., or below about 1° C., or below about 0° C. Separating may be performed at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C., in some embodiments.

According to some embodiments, a process for growing, harvesting, and separating a microcrop (e.g., aquatic plant species, *Lemna*, algal species) may comprise a single cycle. In a single cycle process, in some embodiments, at least one of a first cake (e.g., 240) and a second cake (e.g., 246) may be combined with a first solid to form a solid mixture, and the solid mixture may be further processed (e.g., FIGS. 2A, 2B, 2C). In some embodiments of a single cycle process, a third juice may be combined with a first juice prior to further processing.

In some embodiments a process for growing, harvesting, and separating a microcrop (e.g., aquatic plant species, *Lemna*, algal species) may comprise multiple cycles (e.g., a continuous process). In a multiple cycle or continuous process, according to some embodiments, one or more of a first cake (e.g., 240) and a second cake (e.g., 246) that are collected in an earlier cycle may be combined with a solid fraction from a subsequent cycle prior to separation of the solid fraction. In some embodiments of a multiple cycle or continuous process a third juice collected in an earlier cycle may be combined with a juice fraction from a subsequent cycle prior to further processing.

First Filtration of a First Juice, a Third Juice, or any Combination Thereof

A first juice (e.g., first portion, second portion), a third juice (e.g., first portion, second portion), or any combination thereof may be filtered (e.g., first filtration 246) one or more times to generate a first soluble protein (e.g., 250). A first filtration involve microfiltration, ultrafiltration, nanofiltration, or reverse osmosis filtration either individually or in combination.

Microfiltration may reduce the concentration of suspended solids (e.g., fats, fiber), microbial contamination (e.g., *Escherichia coli*), and/or fungal contamination (e.g., yeast) in a first juice, a third juice, or any combination thereof, according to some embodiments. In some embodiments, a first soluble protein produced by microfiltration may have a reduced oxalic acid content. Suitable filter sizes for microfiltration may include, in some embodiments, ≤about 10 µm, or ≤about 5 µm, or ≤about 3 µm, or ≤about 2 µm, or ≤about 1 µm, or ≤about 0.5 µm, or ≤about 0.4 µm, or ≤about 0.3 µm, or ≤about 0.2 µm, or ≤about 0.1 µm. In some embodiments, a first juice, a third juice, or any combination thereof may be filtered using microfiltration to generate a soluble protein in the permeate.

Ultrafiltration may involve membrane filtration using pressure, concentration gradients, or a combination thereof. Suitable nominal molecular weight cut-offs (NMWCO) for ultrafiltration may be, in some embodiments, at most about 100 kDa, or at most about 90 kDa, or at most about 80 kDa, or at most about 70 kDa, or at most about 60 kDa, or at most about 55 kDa, or at most about 50 kDa, or at most about 45 kDa, or at most about 40 kDa, or at most about 30 kDa, or at most about 20 kDa, or at most about 15 kDa, or at most about 14 kDa, or at most about 13 kDa, or at most about 12 kDa, or at most about 11 kDa, or at most about 10 kDa, or at most about 9 kDa, or at most about 8 kDa, or at most about 7 kDa, or at most about 6 kDa, or at most about 5 kDa, or at most about 4 kDa, or at most about 3 kDa, or at most about 2 kDa, or at most about 1 kDa. In some embodiments, suitable NMWCO cut-offs for ultrafiltration may be in a range of at most about 1 kDa to at most about 10 kDa, at most about 2 kDa to at most about 10 kDa, at most about 3 kDa to at most about 10 kDa, at most about 3 kDa to at most about 15 kDa, or at most about 3 kDa to at most about 20 kDa, or at most about 3 kDa to at most about 60 kDa, or at most about 3 kDa to at most about 55 kDa, or at most about 10 kDa to at most about 55 kDa. In some embodiments a NMWCO for ultrafiltration may be at least 1 kDa, or at least 3 kDa, or at least 5 kDa, or at least 10 kDa, or at least 15 kDa, or at least 20 kDa, or at least 25 kDa, or at least 30 kDa, or at least 35 kDa, or at least 40 kDa, or at least 45 kDa, or at least 50 kDa, or at least 55 kDa. A suitable NMWCO for ultrafiltration may vary depending on a manufacturing specification of an ultrafilter. In some embodiments a suitable NMWCO for ultrafiltration may vary depending on a rate of hydrolysis.

In some embodiments, suitable filter sizes for nanofiltration may include ≤about 0.01 µm, or ≤about 0.009 µm, or ≤about 0.008 µm, or ≤about 0.007 µm, or ≤about 0.006 µm, or ≤about 0.005 µm, or ≤about 0.004 µm, or ≤about 0.003 µm, or ≤about 0.002 µm, or ≤about 0.001 µm. A nanofiltration filter may have a filter size of not more than about 0.01 µm, in some embodiments.

According to some embodiments, suitable filter sizes for reverse osmosis filtration may include ≤about 0.001 µm, ≤about 0.0009 µm, ≤about 0.0008 µm, ≤about 0.0007 µm, ≤about 0.0006 µm, ≤about 0.0005≤about 0.0004 µm, ≤about 0.0003 µm, ≤about 0.0002 µm, or ≤about 0.0001 µm. A reverse osmosis filter may have a filter size of not more than about 0.001 µm, in some embodiments.

Buffers, protease inhibitors, anti-microbial agents, chelators (e.g., EDTA), reducing agents, or any combination thereof may be added, in some embodiments, to a first soluble protein product. A first soluble protein product may be chilled and/or stored at a temperature below about 30° C., or below about 25° C., or below about 20° C., or below about 15° C., or below about 10° C., or below about 5° C., or below about 2° C., or below about 1° C., or below about 0° C., or below about −2° C., or below about −5° C., or below about −10° C., in some embodiments. Chilling and/or storing a soluble protein product at reduced temperatures may reduce degradation and/or improve protein recovery efficiency.

Second Filtration of a First Soluble Protein

According to some embodiments, a first soluble protein (e.g., 246) may be subjected to a second filtration (e.g., 252) to form a second soluble protein (e.g., 256) and a second reject stream (e.g., 254). A second filtration may include ultrafiltration, nanofiltration, and/or reverse osmosis filtration.

Ultrafiltration may involve membrane filtration using pressure, concentration gradients, or a combination thereof. Suitable nominal molecular weight cut-offs (NMWCO) for ultrafiltration may be, in some embodiments, at most about 100 kDa, or at most about 90 kDa, or at most about 80 kDa, or at most about 70 kDa, or at most about 60 kDa, or at most about 55 kDa, or at most about 50 kDa, or at most about 45 kDa, or at most about 40 kDa, or at most about 30 kDa, or at most about 20 kDa, or at most about 15 kDa, or at most about 14 kDa, or at most about 13 kDa, or at most about 12 kDa, or at most about 11 kDa, or at most about 10 kDa, or at most about 9 kDa, or at most about 8 kDa, or at most about 7 kDa, or at most about 6 kDa, or at most about 5 kDa, or at most about 4 kDa, or at most about 3 kDa, or at most about 2 kDa, or at most about 1 kDa. In some embodiments, suitable NMWCO cut-offs for ultrafiltration may be in a range of at most about 1 kDa to at most about 10 kDa, at most about 2 kDa to at most about 10 kDa, at most about 3 kDa to at most about 10 kDa, at most about 3 kDa to at most about 15 kDa, or at most about 3 kDa to at most about 20 kDa, or at most about 3 kDa to at most about 60 kDa, or at most about 3 kDa to at most about 55 kDa, or at most about 10 kDa to at most about 55 kDa. In some embodiments a NMWCO for ultrafiltration may be at least 1 kDa, or at least 3 kDa, or at least 5 kDa, or at least 10 kDa, or at least 15 kDa, or at least 20 kDa, or at least 25 kDa, or at least 30 kDa, or at least 35 kDa, or at least 40 kDa, or at least 45 kDa, or at least 50 kDa, or at least 55 kDa. A suitable NMWCO for ultrafiltration may vary depending on a manufacturing specification of an ultrafilter. In some embodiments a suitable NMWCO for ultrafiltration may vary depending on a rate of hydrolysis.

In some embodiments, suitable filter sizes for nanofiltration may include ≤about 0.01 µm, or ≤about 0.009 µm, or ≤about 0.008 µm, or ≤about 0.007 µm, or ≤about 0.006 µm, or ≤about 0.005 µm, or ≤about 0.004 µm, or ≤about 0.003 µm, or ≤about 0.002 µm, or ≤about 0.001 µm. A nanofiltration filter may have a filter size of not more than about 0.01 µm, in some embodiments.

According to some embodiments, suitable filter sizes for reverse osmosis filtration may include ≤about 0.001 µm, ≤about 0.0009 µm, ≤about 0.0008 µm, ≤about 0.0007 µm, ≤about 0.0006 µm, ≤about 0.0005≤about 0.0004 µm, ≤about 0.0003 µm, ≤about 0.0002 µm, or ≤about 0.0001 µm. A reverse osmosis filter may have a filter size of not more than about 0.001 µm, in some embodiments.

Buffers, protease inhibitors, anti-microbial agents, chelators (e.g., EDTA), reducing agents, or any combination thereof may be added, in some embodiments, to a second soluble protein product. A second soluble protein product may be chilled and/or stored at a temperature below about 30° C., or below about 25° C., or below about 20° C., or below about 15° C., or below about 10° C., or below about 5° C., or below about 2° C., or below about 1° C., or below about 0° C., or below about –2° C., or below about –5° C., or below about –10° C., in some embodiments. Chilling and/or storing a second soluble protein product at reduced temperatures may reduce degradation and/or improve protein recovery efficiency.

Reducing a Moisture Content of Soluble Protein Products

In some embodiments a process may be used to reduce a moisture content of a first soluble protein (e.g., 250), a second soluble protein (e.g., 256), or any combination thereof (collectively "a soluble protein product"). Reducing a moisture content of a soluble protein product may reduce capital and operational expenditures, for example, by reducing the energy needed to dry an end protein product (e.g., concentrated soluble protein with reduced oxalic acid 262).

In some embodiments an evaporation process may be used to reduce a moisture content of a soluble protein product to form a concentrated protein product (e.g., concentrated protein product with reduced oxalic acid 262). Evaporation may be performed by, for example, a thermal (evaporative) means such as: a rising film evaporator, a falling film evaporator, a natural circulation evaporator (vertical or horizontal), an agitated-film evaporator, a multiple-effect evaporator, by vacuum evaporation, or any combination thereof. Heat may be supplied directly into the evaporator, or indirectly through a heat jacket. Heat may either come from a raw source (e.g., combustion of natural gas, steam from a boiler) or from a waste heat stream (e.g., dryer exhaust) or from heat transferred by cooling the input stream.

A moisture content of a soluble protein product (e.g., a second soluble protein) may be reduced, in some embodiments, by nanofiltration or reverse osmosis filtration (e.g., 258) to form a concentrated protein product (e.g., concentrated protein product with reduced oxalic acid 262). In some embodiments, suitable filter sizes for nanofiltration may include ≤about 0.01 µm, or ≤about 0.009 µm, or ≤about 0.008 µm, or ≤about 0.007 µm, or ≤about 0.006 µm, or ≤about 0.005 µm, or ≤about 0.004 µm, or ≤about 0.003 µm, or ≤about 0.002 µm, or ≤about 0.001 µm. A moisture content of a soluble protein product (e.g., a second soluble protein) may be reduced, in some embodiments, using nanofiltration with the soluble protein product (e.g., concentrated protein product with reduced oxalic acid 262) in a retentate. According to some embodiments, suitable filter sizes for reverse osmosis filtration may include ≤about 0.001 µm, ≤about 0.0009 µm, ≤about 0.0008 µm, ≤about 0.0007 µm, ≤about 0.0006 µm, ≤about 0.0005≤about 0.0004 µm, ≤about 0.0003 µm, ≤about 0.0002 µm, or ≤about 0.0001 µm. A moisture content of a soluble protein product (e.g., a second soluble protein), in some embodiments, may be reduced using reverse osmosis filtration with the soluble protein product (e.g., concentrated protein product with reduced oxalic acid 262) in a retentate. A permeate of nanofiltration or reverse osmosis filtration may be recycled (e.g., dilution fluid for lysis 260; wash solution), according to some embodiments.

In some embodiments an antioxidant (e.g., rosemary extract) may be mixed with a soluble protein product (e.g., a second soluble protein 256, concentrated protein product with reduced oxalic acid 262) prior to drying to improve shelf life of product when packaged.

Polyphenol Reduction

In some embodiments, a polyphenol-rich product may be subjected to a polyphenol reduction process to generate a product having a reduced concentration of at least one polyphenol (e.g., a tannin). A polyphenol-rich product may include, according to some embodiments, a juice fraction (e.g., FIGS. 1A, 1B, 1C, 1D, 126; FIGS. 2A, 2B, 2B, 226), a first soluble protein (e.g., FIGS. 2A, 2B, 2C, 250), a second soluble protein (e.g., FIGS. 2A, 2B, 2C, 256), a concentrated protein product with reduced oxalic acid (e.g., FIGS. 2A, 2B, 2C, 262, a first juice (e.g., FIGS. 2A, 2B, 2C, 238), a second juice (e.g., FIGS. 2A, 2B, 2C, 232), a third juice (e.g., FIG. 2A, 2B, 2C, 244), or any combination thereof. A polyphenol reduction process may be configured to reduce a concentration of at least one polyphenol (e.g., at least one tannin), according to some embodiments. A polyphenol reduction process may be configured, in some embodiments, to minimize a reduction in yield or quality of a downstream soluble protein product.

According to some embodiments a polyphenol reduction process may comprise passing a polyphenol-rich product through an ion exchange resin. In some embodiments, a polyphenol reduction process may comprise passing a polyphenol-rich product through a series (e.g., at least two, at least three) of ion exchange resins. Each ion exchange resin in a series may be the same or different than the other ion exchange resins in the series. In some embodiments an ion exchange resin may be a strongly acidic resin, a strongly basic resin (e.g., DIAION PA308), a weakly acidic resin (e.g., Relite JA800), a weakly basic resin, a weak anion exchange resin (e.g., Relite RAM2), a strong anion exchange resin, a weak cation exchange resin, a strong cation exchange resin, or any combination thereof. According to some embodiments a polyphenol reduction process may comprise passing a polyphenol-rich product through an ion exchange column selected from a weakly acidic resin (e.g., Relite JA800), an anion exchange resin (e.g., Relite RAM2), a strongly basic resin (e.g., DIAION PA308), or a combination thereof. A polyphenol reduction process, in some embodiments, may comprise: first passing a polyphenol-rich product through an ion exchange column selected from a weak anion exchange and a strong anion exchange resin, and second passing the polyphenol-rich product through an ion exchange column selected from a weak anion exchange resin and a strong anion exchange resin. Ion exchange resins may be used in a batch mode or arranged in a continuous process, whereby resins may be cycled through polyphenol extraction and regeneration processes. In some embodiments a polyphenol reduction process may further comprise adjusting a pH of a polyphenol-rich product or a product yielded from an ion exchange column. A polyphenol reduction process may be performed alone or in combination with other purification processes and/or steps.

In some embodiments a polyphenol reduction process may reduce a polyphenol (e.g., a tannin) content of a polyphenol-rich product by at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%. A polyphenol reduction process, according to some embodiments, may reduce a polyphenol content of a polyphenol-rich product from about 5% to about 10%, from about 15% to about 20%, from about 20% to about 30%, from about 30% to about 40%, from about 35% to about 45%, from about 40% to about 50%, from about 45% to about 55%, from about 50% to about 60%, from about 55% to about 65%, or from about 60% to about 70%.

In some embodiments, a soluble protein product (e.g., a soluble protein, a first soluble protein, a second soluble protein), may comprise polyphenol (e.g., total polyphenol) at a concentration of about 0.05 g/100 g of soluble protein product, about 0.1 g/100 g of soluble protein product, about 0.5 g/100 g of soluble protein product, about 1 g/100 g of soluble protein product, about 5 g/100 g of soluble protein product, about 10 g/100 g of soluble protein product, and about 20 g/100 g of protein concentrate. According to some embodiments, based on analysis of a pasteurized product, a 100 g of a final product may contain about 65 g of protein and about 1.092 g polyphenols (expressed as gallic acid equivalents).

Drying a Soluble Protein Product

A soluble protein product (e.g., a first soluble protein 250, a second soluble protein 256, concentrated protein product with reduced oxalic acid 262) may be dried to generate a dry protein concentrate (e.g., first portion, second portion), according to some embodiments. A drying procedure (e.g., 264), in some embodiments, may reduce the moisture content of a soluble protein product to a desired level (e.g., higher or lower moisture content, a desired moisture content). A moisture content of a dry protein concentrate may be, for example, below 90%, or below about 80%, or below about 70%, or below about 60%, or below about 50%, or below about 40%, or below about 30%, or below about 20%, or below about 10%, or below about 5%, or below about 1% by weight of the dry protein concentrate, in some embodiments. According to some embodiments, a protein concentration of a dry protein concentrate may be from about 30% to about 95%, or from about 40% to about 90%, or from about 50% to about 85%, or from about 60% to about 80%, or from about 70% to about 75% by weight of the dry protein concentrate. A drying procedure may be performed using a mechanism including, for example, a spray dryer, double drum dryer, flash dryer, an evaporator, or any combination thereof.

In some embodiments, an inlet temperature of a dryer mechanism (the temperature at the entrance to a dryer) may be above 25° C., or above 50° C., or above 75° C., or above 100° C., or above 125° C., or above 150° C., or above 175° C., or above 200° C., or above 225° C., or above 250° C., or above 275° C., or above 300° C., or above 325° C., or above 350° C., or above 375° C., or above 400° C., or above 425° C., or above 450° C., or above 475° C., or above 500° C. An inlet temperature, in some embodiments, may be from about 25° C. to about 50° C., or from about 50° C. to about 75° C., or from about 75° C. to about 100° C., or from about 100° C. to about 125° C., or from about 125° C. to about 150° C., or from about 150° C. to about 175° C., or from about 175° C. to about 200° C., or from about 200° C. to about 225° C., or from about 225° C. to about 250° C., or from about 250° C. to about 275° C., or from about 275° C. to about 300° C., or from about 300° C. to about 325° C., or from about 325° C. to about 350° C., or from about 350° C. to about 375° C., or from about 375° C. to about 400° C., or from about 400° C. to about 425° C., or from about 425° C. to about 450° C., or from about 450° C. to about 475° C., or from about 475° C. to about 500° C., or above 500° C. An inlet temperature may be from about 50° C. to about 100° C., or from about 100° C. to about 150° C., or from about 150° C. to about 200° C., or from about 200° C. to about 250° C., or from about 250° C. to about 300° C., or from about 300° C. to about 350° C., or from about 350° C. to about 400° C., or from about 400° C. to about 450° C., or from about 450° C. to about 500° C., or above 500° C., in some embodiments. According to some embodiments, an inlet temperature of a dryer mechanism may be about 225° C.

According to some embodiments, an outlet temperature of a dryer mechanism (the temperature at the exit from a dryer) may be below about 300° C., or below about 275° C., or below about 250° C., or below about 225° C., or below about 200° C., or below about 175° C., or below about 150° C., or below about 125° C., or below about 100° C., or below about 75° C., or below about 50° C., or below about 25° C. An outlet temperature may be from about 300° C. to about 275° C., or from about 275° C. to about 250° C., or from about 250° C. to about 225° C., or from about 225° C. to about 200° C., or from about 200° C. to about 175° C., or from about 175° C. to about 150° C., or from about 150° C. to about 125° C., or from about 125° C. to about 100° C., or from about 100° C. to about 75° C., or from about 75° C. to about 50° C., or from about 50° C. to about 25° C., or below about 25° C., in some embodiments. An outlet temperature, in some embodiments, may be from about 300° C. to about 250° C., or from about 250° C. to about 200° C., or from about 200° C. to about 150° C., or from about 150° C. to about 100° C., from about 100° C. to about 50° C., or from about 50° C. to about 25° C., or below about 25° C. According to some embodiments, an outlet temperature of a dryer mechanism may be about 75° C.

In some embodiments, a volume of a soluble protein product (e.g., a first soluble protein 250, a second soluble protein 256, concentrated protein product with reduced oxalic acid 262) may be mixed with a volume of a dry protein concentrate prior to drying. This process, known as back-mixing, may be employed when, for example, the moisture content of a soluble protein exceeds the level that a dryer mechanism is capable of accepting. By back-mixing a dry protein concentrate with a soluble protein product, a total moisture content may be kept within the specifications of a dryer mechanism, thereby reducing operational costs (e.g., wear and tear on equipment).

An antioxidant (e.g., rosemary extract) may be mixed with a dry protein concentrate before packaging, according to some embodiments.

Solvent Washing a Soluble Protein Product or a Dry Protein Concentrate

A soluble protein product (e.g., a soluble protein, a first soluble protein 250, a second soluble protein 256) and/or a concentrated protein product with reduced oxalic acid (e.g., 262) may be washed with at least one solvent (e.g., ethanol, methanol) to generate a washed protein product, according to some embodiments.

A washed protein product, in some embodiments, may have a reduced fat content (e.g., about 2% of a dry protein concentrate or less by weight) and/or a reduced chlorophyll content (e.g., visually perceivable reduction in green coloration) compared to unwashed counterparts. In some embodiments, a washed protein product may appear colorless, white, substantially white, or have reduced green coloration. A washed protein product, in some embodiments, may exhibit improved taste, color, shelf life (e.g., reduced oxidation of fats), protein density, malleability, and combinations thereof. In some embodiments, a washed protein product may be extruded to form a texturized protein product.

According to some embodiments, a solvent may comprise methanol, ethanol, acetone, hexane, dichloromethane, ethyl acetate, propanol, isopropanol, glycerol, or combinations thereof.

In some embodiments, a washed protein product may have a fat content comprising less than about 50%, or less than about 40%, or less than about 30%, or less than about 25%, or less than about 20%, or less than about 15%, or less than about 10%, or less than about 5%, or less than about 4%, or less than about 3%, or less than about 2%, or less than about 1% by weight of the washed protein product. According to some embodiments, a washed protein product may have a fat content comprising from about 1% to about 10%, or from about 10% to about 20%, or from about 20% to about 30%, or from about 30% to about 40%, or from about 40% to about 50% by weight of the protein concentrate in some embodiments.

In some embodiments, a washed protein product may have a fat content comprising about 15% of a dry protein concentrate or less by weight, about 10% of a dry protein concentrate or less by weight, about 8% of a dry protein concentrate or less by weight, about 6% of a dry protein concentrate or less by weight, about 4% of a dry protein concentrate or less by weight, about 2% of a dry protein concentrate or less by weight, about 1% of a dry protein concentrate or less by weight, about 0.5% of a dry protein concentrate or less by weight, about 0.2% of a dry protein concentrate or less by weight, or about 0.1% of a dry protein concentrate or less by weight. In some embodiments, a washed protein product may have a fat content comprising from about 0.1 to about 0.2% by weight of a dry protein concentrate.

Protein Concentrate

Some embodiments relate to a process for production of a soluble protein product (e.g., a first soluble protein 250, a second soluble protein 256, concentrated protein product with reduced oxalic acid 262) and/or a dry protein concentrate (collectively "a protein concentrate") from a biomass of a harvested microcrop (e.g., aquatic plant species, Lemna, algal species). A process may be configured or performed to achieve any desired protein yield (e.g., maximal yield, a selected yield). In some embodiments, a protein concentration of a protein concentrate is higher than about 30%, or higher than about 40%, or higher than about 50%, or higher than 55%, or higher than about 60%, or higher than 65%, or higher than about 70%, or higher than about 75%, or higher than about 80% by weight of the protein concentrate. A remainder of a protein concentrate may include carbohydrates, fiber, fats, minerals, or any combination thereof. A protein concentrate is suitable for animal feed and/or human consumption. For example, a protein concentrate may serve as an effective replacement for protein isolates (e.g., soy, pea, whey) which are presently used in a large number of human food products either individually or as ingredients and additives. According to some embodiments, a protein composition of a protein concentrate may be in native or near native form. For example, a protein composition of a protein concentrate may include <2% denatured protein, or <4% denatured protein, <6% denatured protein, or <8% denatured protein, or <10% denatured protein, or <15% denatured protein, or <20% denatured protein, or <25% denatured protein, or <30% denatured protein, or <35% denatured protein, or <40% denatured protein, or <45% denatured protein, or <50%.

In some embodiments, a protein concentrate may comprise one or more essential amino acids. For example, a protein concentrate may include one or more amino acids selected from leucine, isoleucine, lysine, methionine, phenylalanine, threonine, tryptophan, valine, histidine, arginine, aspartic acid, serine, glutamic acid, proline, glycine, alanine, tyrosine and cysteine. The concentration of an essential amino acid may be at least about 1 g/100 g of protein concentrate, or at least about 1.5 g/100 g of protein concentrate, or at least about 2 g/100 g of protein concentrate, or at least about 2.5 g/100 g of protein concentrate, or at least about 3 g/100 g of protein concentrate, or at least about 4 g/100 g of dry at least about 2.5 g/100 g of protein concentrate, or at least about 3 g/100 g of protein concentrate, or at least about 4 g/100 g of protein concentrate, or at least about 5 g/100 g of protein concentrate, or at least about 6 g/100 g of protein concentrate, or at least about 7 g/100 g of protein concentrate, or at least about 8 g/100 g of protein concentrate, or at least about 9 g/100 g of protein concentrate, or at least about 10 g/100 g of protein concentrate in some embodiments.

The concentration of an amino acid (e.g., an essential amino acid), in some embodiments, may be expressed as a weight fraction of the protein recovered from a protein concentrate, and is at least about 1 g/100 g of protein, or at least about 1.5 g/100 g of protein, or at least about 2 g/100 g of protein, or at least about 2.5 g/100 g of protein, or at least about 3 g/100 g of protein, or at least about 4 g/100 g of protein, or at least about 5 g/100 g of protein, or at least about 6 g/100 g of protein, or at least about 7 g/100 g of protein, or at least about 8 g/100 g of protein, or at least about 9 g/100 g of protein, or at least about 10 g/100 g of protein.

In some embodiments, a protein concentrate may comprise one or more branched-chain amino acids (BCAAs). For example, a protein concentrate may include one or more amino acids selected from leucine, isoleucine, valine, and combinations thereof. A concentration of a BCAA may be at least about 1 g/100 g of protein concentrate, or at least about 1.5 g/100 g of protein concentrate, or at least about 2 g/100 g of protein concentrate, or at least about 2.5 g/100 g of protein concentrate, or at least about 3 g/100 g of protein concentrate, or at least about 4 g/100 g of dry at least about 2.5 g/100 g of protein concentrate, or at least about 3 g/100 g of protein concentrate, or at least about 4 g/100 g of protein concentrate, or at least about 5 g/100 g of protein concentrate, or at least about 6 g/100 g of protein concentrate, or at least about 7 g/100 g of protein concentrate, or at least about 8 g/100 g of protein concentrate, or at least about 9 g/100 g of protein concentrate, at least about 10 g/100 g of protein concentrate, at least about 11 g/100 g of protein concentrate, at least about 12 g/100 g of protein concentrate, at least about 13 g/100 g of protein concentrate, at least about 14 g/100 g of protein concentrate, or at least about 15 g/100 g of protein concentrate in some embodiments. In some embodiments, a BCAA protein content of a protein concentrate is higher than about 10%, or higher than about 11%, higher than about 12%, higher than about 13%, higher than about 14%, higher than about 15%, or higher than about 20%, or higher than about 25%, or higher than about 30%, or higher than 35%, or higher than about 40%, or higher than 45%, or higher than about 50%, or higher than about 55%, or higher than about 60% of total amino acids of a protein concentrate. In some embodiments, it has been found that a BCAA content of a protein rich product is 20-21% of a total amino acid content, about 11% higher than a BCAA content of an alternative protein products derived from pea or soybeans which contain about 18-19% of a total amino acid content (e.g., an increase from 18% to 20% is an 11% increase). According to some embodiments, a BCAA protein content may be evaluated using ion exchange chromatography of an amino acid profile based on the Association of Official Agricultural Chemists (AOAC) Official Method 994.12.

According to some embodiments, a protein concentrate may have an oxalic acid ($H_2C_2O_4$ or HOOCCOOH) content that is reduced relative to a method that comprises neither (a) cultivating a microcrop in an increased calcium first medium, nor (b) cultivating a microcrop in a first medium comprising one or more anti-photosynthetic dyes, nor (c) soaking, nor (d) buffering, nor (e) precipitating calcium oxalate from a lysed biomass, nor (0 precipitating calcium oxalate from a first juice, nor (g) filtering a first juice, nor any combination thereof. In some embodiments, a protein concentrate (e.g., soluble microcrop protein) may have an oxalic acid content (wherein total oxalic acid content is calculated on a dry mass basis (DMB)) of less than about 0.6% DMB, less than about 0.55% DMB, less than about 0.5% DMB, or less than about 0.45% DMB, or less than about 0.4% DMB, or less than about 0.35% DMB, or less than about 0.3% DMB, or less than about 0.25% DMB, or less than about 0.2% DMB, or less than about 0.15% DMB, or less than about 0.1% DMB, or less than about 0.05% DMB, or less than about 0.04% DMB, or less than about 0.03% DMB, or less than about 0.02% DMB. A protein concentrate, in some embodiments may have an oxalic acid content of from about 0.02% DMB to about 0.6% DMB, or from about 0.02% DMB to about 0.5% DMB, or from about 0.02% DMB to about 0.4% DMB, or from about 0.02% DMB to about 0.3% DMB, or from about 0.02% DMB to about 0.2% DMB, or from about 0.02% DMB to about 0.15% DMB, or from about 0.02% DMB to about 0.1% DMB. In some embodiments, a protein concentrate may have an oxalic acid content of no more than 0.1% DMB. According to some embodiments, a protein concentrate may have an oxalic acid content (e.g., total oxalic acid content) of no more than 0.05% DMB.

According to some embodiments, a protein concentrate may also have an oxalate ($C_2O_4^{2-}$) content that is reduced relative to a method that comprises neither (a) cultivating a microcrop in an increased calcium first medium, nor (b) cultivating a microcrop in a first medium comprising one or more anti-photosynthetic dyes, nor (c) soaking, nor (d) buffering, nor (e) precipitating calcium oxalate from a lysed biomass, nor (f) precipitating calcium oxalate from a first juice, nor (g) microfiltering a first juice, nor any combination thereof.

In some embodiments, a protein concentrate may have a fat content less than about 50%, or less than about 40%, or less than about 30%, or less than about 25%, or less than about 20%, or less than about 15%, or less than about 10%, or less than about 5%, or less than about 4%, or less than about 3%, or less than about 2%, or less than about 1% by weight of the protein concentrate. A protein concentrate may have a fat content from about 1% to about 10%, or from about 10% to about 20%, or from about 20% to about 30%, or from about 30% to about 40%, or from about 40% to about 50% by weight of the protein concentrate in some embodiments. A protein concentrate, in some embodiments, may have a fat content from about 1% to about 50%, or from about 2% to about 40%, or from about 5% to about 30%, or from about 8% to about 20%, or from about 10% to about 15% by weight of the protein concentrate. A protein concentrate may be further processed to meet a desired fat content (e.g., higher or lower concentration, a desired fat composition).

According to some embodiments, a protein concentrate may include an ash content consisting of a residue containing inorganic mineral elements. An ash content in some embodiments may be determined by combusting a protein concentrate at a high temperature (e.g., ≥500° C.) to remove organic matter. A protein concentrate may have an ash content less than about 50%, or less than about 40%, or less than about 30%, or less than about 25%, or less than about 20%, or less than about 15%, or less than about 10%, or less than about 5%, or less than about 4%, or less than about 3%, or less than about 2%, or less than about 1% by weight of the protein concentrate in some embodiments. In some embodiments, a protein concentrate may have an ash content from about 1% to about 10%, or from about 10% to about 20%, or from about 20% to about 30%, or from about 30% to about 40%, or from about 40% to about 50% by weight of the protein concentrate. A protein concentrate, in some embodiments, may have an ash content from about 1% to about 50%, or from about 2% to about 40%, or from about 3% to about 30%, or from about 3% to about 20%, or from about 3% to about 15%, or from about 3% to about 10%, or from about 5% to about 10%, or from about 5% to about 15% by weight of the protein concentrate. A protein concentrate may be further processed to meet a desired ash content (e.g., higher or lower concentration, a desired ash composition).

According to some embodiments, a protein concentrate may have a carbohydrate content less than about 50%, or less than about 40%, or less than about 30%, or less than about 25%, or less than about 20%, or less than about 15%, or less than about 10%, or less than about 5%, or less than about 4%, or less than about 3%, or less than about 2%, or less than about 1% by weight of the protein concentrate. A protein concentrate, in some embodiments, may have a carbohydrate content from about 1% to about 10%, or from about 10% to about 20%, or from about 20% to about 30%, or from about 30% to about 40%, or from about 40% to about 50% by weight of the protein concentrate. In some embodiments, a protein concentrate may have a carbohydrate content from about 1% to about 50%, or from about 2% to about 40%, or from about 5% to about 30%, or from about 8% to about 20%, or from about 10% to about 15% by weight of the protein concentrate. A protein concentrate may be further processed to meet a desired carbohydrate content (e.g., higher or lower concentration, a desired carbohydrate composition).

In some embodiments, a protein concentrate may have a fiber content less than about 20%, or less than about 15%, or less than about 10%, or less than about 8%, or less than about 5%, or less than about 4%, or less than about 3%, or less than about 2%, or less than about 1% by weight of the protein concentrate. A protein concentrate may be further processed to meet a desired fiber content (e.g., higher or lower concentration, a desired fiber composition).

For example, a dry protein concentrate produced by the processes described herein may include the contents summarized in Table 2.

TABLE 2

Example Contents of Dry Protein Concentrate Product

| Wt. Percent | Product 1 | Product 2 | Product 3 |
|---|---|---|---|
| Solids | ≥~90 | ≥~88-~90 | ≥~95 |
| Moisture | ≤~10 | ≤~12-~10 | ≤~5 |
| Protein | ≥~50 | from ~60 to ~80 | ≥~65-~75 |
| Fat | ≤~20 | from ~5 to ~20 | ≤~5-~15 |
| Ash | ≤~15 | from ~1 to ~10 | ≤~2-~10 |
| Carbohydrate | ≤~20 | from ~5 to ~20 | ≤~10-~15 |
| Fiber | ≤~10 | ≤~5 | ≤~5 |
| Oxalic Acid | ≤0.05% | ≤0.1% | ≤0.05% |
| Other | ~10 | ~5-~20 | ~10-~15 |

A product and/or process, in some embodiments, may be configured or performed so other characteristics of a protein concentrate, (e.g., particle size, bacterial specification) meet desired criteria and/or may be suitable for an intended purpose.

According to some embodiments a protein concentrate may have a mesh size (e.g., most or all gross particles of the protein concentrate will pass through a mesh having an average pore size) of about 30 µm, or about 40 µm, or about 50 µm, or about 60 µm, or about 70 µm, or about 80 µm, or about 90 µm, or about 100 µm, or about 110 µm, or about 120 µm, or about 130 µm, or about 140 µm, or about 150 µm, or about 160 µm, or about 170 µm, or about 180 µm, or about 190 µm, or about 200 µm, or about 225 µm, or about 250 µm, or about 275 µm, or about 300 µm, or about 325 µm, or about 350 µm, or about 375 µm, or about 400 µm, or about 425 µm, or about 450 µm, or about 475 µm, or about 500 µm. A protein concentrate may have mesh size range of, in some embodiments, about 30 µm to about 500 µm, or about 30 µm to about 300 µm, or about 50 µm to about 300 µm, or about 70 µm to about 300 µm, or about 100 µm to about 300 µm, or about 30 µm to about 200 µm, or about 50 µm to about 200 µm, or about 70 µm to about 200 µm, or about 100 µm to about 200 µm, or about 30 µm to about 190 µm, or about 50 µm to about 190 µm, or about 70 µm or about 190 µm, or about 100 µm to about 190 µm, or about 30 µm to about 180 µm, or about 50 µm to about 180 µm, or about 70 µm to about 180 µm, or about 100 µm to about 180 µm, or about 30 µm to about 170 µm, or about 50 µm to about 170 µm, or about 70 µm to about 170 µm, or about 100 µm to about 170 µm.

A protein concentrate, according to some embodiments may have a density of about 400 kg/m$^3$, or about 405 kg/m$^3$, or about 410 kg/m$^3$, or about 415 kg/m$^3$, or about 420 kg/m$^3$, or about 425 kg/m$^3$, or about 430 kg/m$^3$, or about 435 kg/m$^3$, or about 440 kg/m$^3$, or about 445 kg/m$^3$, or about 450 kg/m$^3$.

In some embodiments a protein concentrate may have a solubility value (% water soluble nitrogen) of at least about 35%, or at least about 40%, or at least about 45%, or at least about 50%, or at least about 55%, or at least about 60%, or at least about 65%, or at least about 70%, or at least about 75%, where "about" in this sentence includes ±5% of the indicated concentration. A solubility value may be determined using the Nitrogen Solubility Index (NSI) method as described in F. Vojdani, *Methods of Testing Protein Functionality* 11-60 (G. M. Hall, ed., 1996).

According to some embodiments, a protein concentrate may have a dispersibility value (% water dispersible protein/% total protein) of at least about 35, or at least about 40, or at least about 45, or at least 50, or at least about 55, or at least about 60, or at least about 65, or at least about 70, or at least about 75 where "about" in this sentence includes ±5. A dispersibility value may be determined using the Protein Dispersibility Index (PDI) as described in F. Vojdani, *Methods of Testing Protein Functionality* 11-60 (G. M. Hall, ed., 1996).

In some embodiments, a standard plate count of bacteria may be less than about 100,000 colony forming unit (cfu)/g, or less than about 80,000 cfu/g, or less than about 60,000 cfu/g, or less than about 50,000 cfu/g, or less than about 40,000 cfu/g, or less than about 30,000 cfu/g, or less than about 25,000 cfu/g, or less than about 20,000 cfu/g, or less than about 15,000 cfu/g, or less than about 10,000 cfu/g, or less than about 5,000 cfu/g, or less than about 1000 cfu/g, or less than about 500 cfu/g. If a protein concentrate comprises any *Escherichia coli*, the bacteria may be present at such low levels as to be undetectable and/or noninfectious. If a protein concentrate comprises any *Salmonella* spp., the bacteria may be present at such low levels as to be undetectable and/or noninfectious. If a protein concentrate comprises any yeast/mold, the microorganism count may be less than about 500/g, or less than about 400/g, or less than about 300/g, or less than about 250/g, or less than about 200/g, or less than about 150/g, or less than about 100/g, or less than about 50/g.

In some embodiments, a protein concentrate may be packed and/or sealed in either an industry standard bag or drum of varying sizes. A sealing method of industry-standard grade may be used to ensure proper shelf-life and shipping conditions. A bag or drum may include printed instructions or specifications regarding, for example, its intended use, shelf-life, suggested storage conditions, shipping conditions, compositions, or the like, or a combination thereof. An antioxidant (e.g., rosemary extract) may be mixed with a protein concentrate before packaging, according to some embodiments.

Processing a First Solid and/or Solid Mixture

A first solid (e.g., first portion, second portion) and/or solid mixture (e.g., first portion, second portion) may be processed to generate one or more carbohydrate-rich products. As described previously, a solid mixture may include one or more of a first solid (e.g., 234), a first cake (e.g., 240), a second cake (e.g., 246), or any combination thereof that remain after one or more separation processes (e.g., 230/236/242). Carbohydrate rich products may include a dry biocrude product suitable as a fuel feedstock, a carbohydrate-rich meal suitable as a human or animal feed supplement (e.g., *Lemna* meal), a product suitable as an odor and/or moisture absorbent (e.g., animal bedding or litter), and polysaccharide products (e.g., apiogalacturonan and/or oligogalacturonide). Methods and systems relating to these products are disclosed in U.S. Provisional Application Nos. 62/173,643; 62/173,645; and 62/189,040 which are incorporated herein by reference.

Heat Exchange

According to some embodiments, thermal energy exchange mechanisms (e.g., heat exchanger) may decrease an overall energy input required for the production of concentrated proteins (e.g., concentrated protein with reduced oxalic acid content) and/or carbohydrate-rich products from a microcrop (e.g., *Lemna*). In some embodiments, a chilled stream (e.g., recipient stream) may be directed to flow in proximity to a donor stream having thermal energy such that the chilled stream absorbs at least some of the donor stream thermal energy. A recipient stream, according to some embodiments, may be directed to flow in proximity to a donor stream having thermal energy such that the recipient stream absorbs at least some of the donor stream thermal energy.

In some embodiments, a recipient stream may be at least one of a lysed biomass (e.g., first portion, second portion), a juice fraction (e.g., first portion, second portion), a first juice (e.g., first portion, second portion), a first soluble protein fraction (e.g., first portion, second portion), a first reject stream, a second soluble protein fraction (e.g., first portion, second portion), a second reject stream, and a permeate. A recipient stream may be a chilled stream, in some embodiments. According to some embodiments at least one of a lysed biomass (e.g., first portion, second portion), a juice fraction (e.g., first portion, second portion), a first juice (e.g., first portion, second portion), a first soluble protein fraction (e.g., first portion, second portion), a first reject stream, a second soluble protein fraction (e.g., first portion, second portion), a second reject stream, and a permeate may be chilled to form a chilled stream. A recipient stream (e.g., a chilled stream) may have a temperature below room temperature (e.g., about 12° C.) at the time of use. In some embodiments, a recipient stream (e.g., a chilled stream) may have a temperature below about 30° C., or below about 20° C., or below about 15° C., or below about 10° C., or below about 5° C., or below about 2° C., or below about 1° C., or below about 0° C. at the time of use. A recipient stream (e.g., a chilled stream) may have a temperature between about 0° C. and about 10° C., or between about 5° C. and about 15° C., or between about 10° C. and about 20° C., or 15° C. and about 25° C., or between about 20° C. and about 30° C. at the time of use, in some embodiments. In some embodiments, a recipient stream (e.g., a chilled stream) may have a temperature of about 12° C. According to some embodiments, a recipient stream (e.g., a chilled stream) may have a temperature that is lower than a donor stream.

A donor stream, in some embodiments, may comprise at least one of a lysed biomass (e.g., first portion, second portion), a juice fraction (e.g., first portion, second portion), or a first juice (e.g., first portion, second portion). According to some embodiments, a donor stream may have a temperature that is higher than a recipient stream. In some embodiments, a donor stream may have a temperature above room temperature (e.g., about 50° C.). In some embodiments, a donor stream may have a temperature above about 20° C., or above about 25° C., or above about 30° C., or above about 35° C., or above about 40° C., or above about 45° C., or above about 50° C., or above about 55° C., or above about 60° C., or above about 65° C., or above about 70° C., or above about 75° C., or above about 80° C., or above about 85° C., or above about 90° C., or above about 95° C., or above about 100° C. at the time of use. A donor stream may have a temperature between about 40° C. and about 50° C., or between about 45° C. and about 55° C., or between about 50° C. and about 60° C. at the time of use, in some embodiments. According to some embodiments, a donor stream may have a temperature between about 75° C. and about 80° C., or between about 80° C. and about 85° C., or between about 85° C. and about 90° C., or between about 90° C. and about 95° C., or between about 95° C. and about 100° C. In some embodiments, a donor stream may have a temperature between about 50° C. and about 80° C., or between about 55° C. and about 85° C., or between about 60° C. and about 90° C., or between about 65° C. and about 95° C., or between about 70° C. and about 100° C.

In some embodiments, a thermal energy may be generated by one or more processes during the production of concentrated proteins and/or carbohydrate-rich products from a microcrop (e.g., *Lemna*). For example, a thermal energy may be generated by (1) drying a concentrated protein, (2) drying a carbohydrate-rich product, and/or (3) chilling at least one of a lysed biomass (e.g., first portion, second portion), a juice fraction (e.g., first portion, second portion), a first juice (e.g., first portion, second portion), a first soluble protein fraction (e.g., first portion, second portion), a first reject stream, a second soluble protein fraction (e.g., first portion, second portion), a second reject stream, and a permeate to generate a chilled stream. According to some embodiments, a thermal energy may be generated in thermal communication with a heat exchanger. For example, chilling at least one of a juice fraction (e.g., first portion, second portion), a first juice (e.g., first portion, second portion), a first soluble protein fraction (e.g., first portion, second portion), a second soluble protein fraction (e.g., first portion, second portion) may be performed in thermal communication with a heat exchanger. Heating at least one of a wash solution, a first reject stream, a second reject stream, and a permeate may be performed in thermal communication with a heat exchanger, in some embodiments. In some embodiments, drying a concentrated protein and/or drying a carbohydrate-rich product may be performed in thermal communication with a heat exchanger.

FIGS. 1A, 1B, 1C, and 1D

FIGS. 1A, 1B, 1C, and 1D are schematic diagrams illustrating a process 100 for growing, harvesting, and separating a microcrop (e.g., aquatic plant species, *Lemna*, algal species) for the production of a protein concentrate having a reduced oxalic acid content according to specific example embodiments of the disclosure.

FIGS. 1A, 1B, 1C, and 1D illustrate example embodiments of a process 100 for the production of a protein concentrate having a reduced oxalic acid content comprising cultivation of a microcrop (e.g., *Lemna*) in a first medium 102. In some embodiments a first medium may comprise an increased calcium first medium (e.g., having a calcium concentration of ≥about 20 ppm to about 120 ppm) and/or one or more anti-photosynthetic dyes. According to some embodiments, the one or more anti-photosynthetic dyes may be added at a sufficient volume or concentration to inhibit growth of at least one other aquatic organism. In some embodiments, the one or more anti-photosynthetic dyes may be added at concentrations of up to 3.5 ppm. The process 100 further comprises harvesting 104 a microcrop. In some embodiment, during harvesting a first medium is separated from a biomass (e.g., static draining, vibratory separator) and at least a portion of the separated first medium may be recycled 106 back into a bioreactor system or to an additional storage container (e.g., container or pond).

Figure 1B:
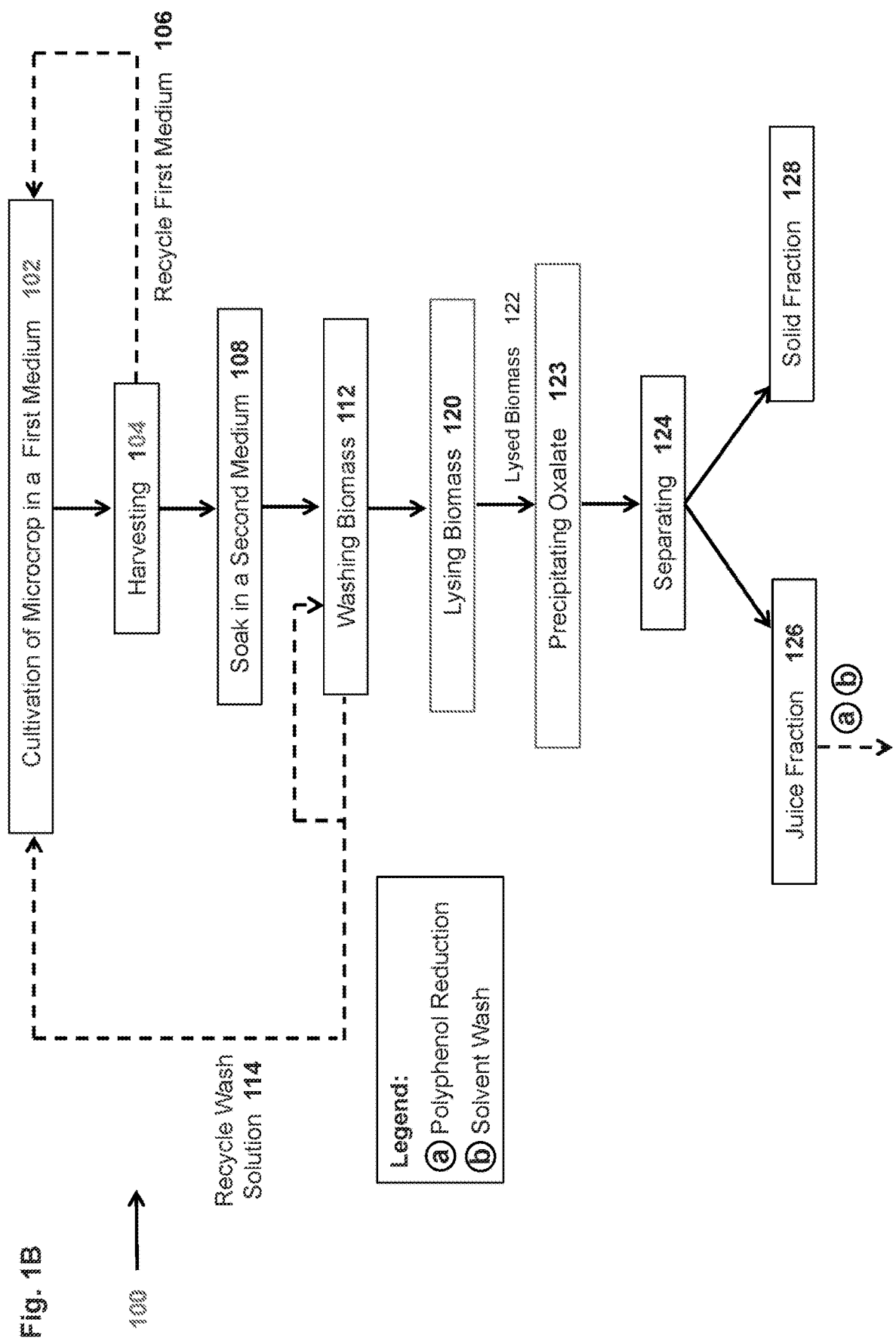
FIG. 1B is a flow diagram illustrating a system for cultivating, harvesting, and processing a microcrop for the production of a protein concentrate having a reduced oxalic acid content according to a specific example embodiment of the disclosure.
Figure 1C:
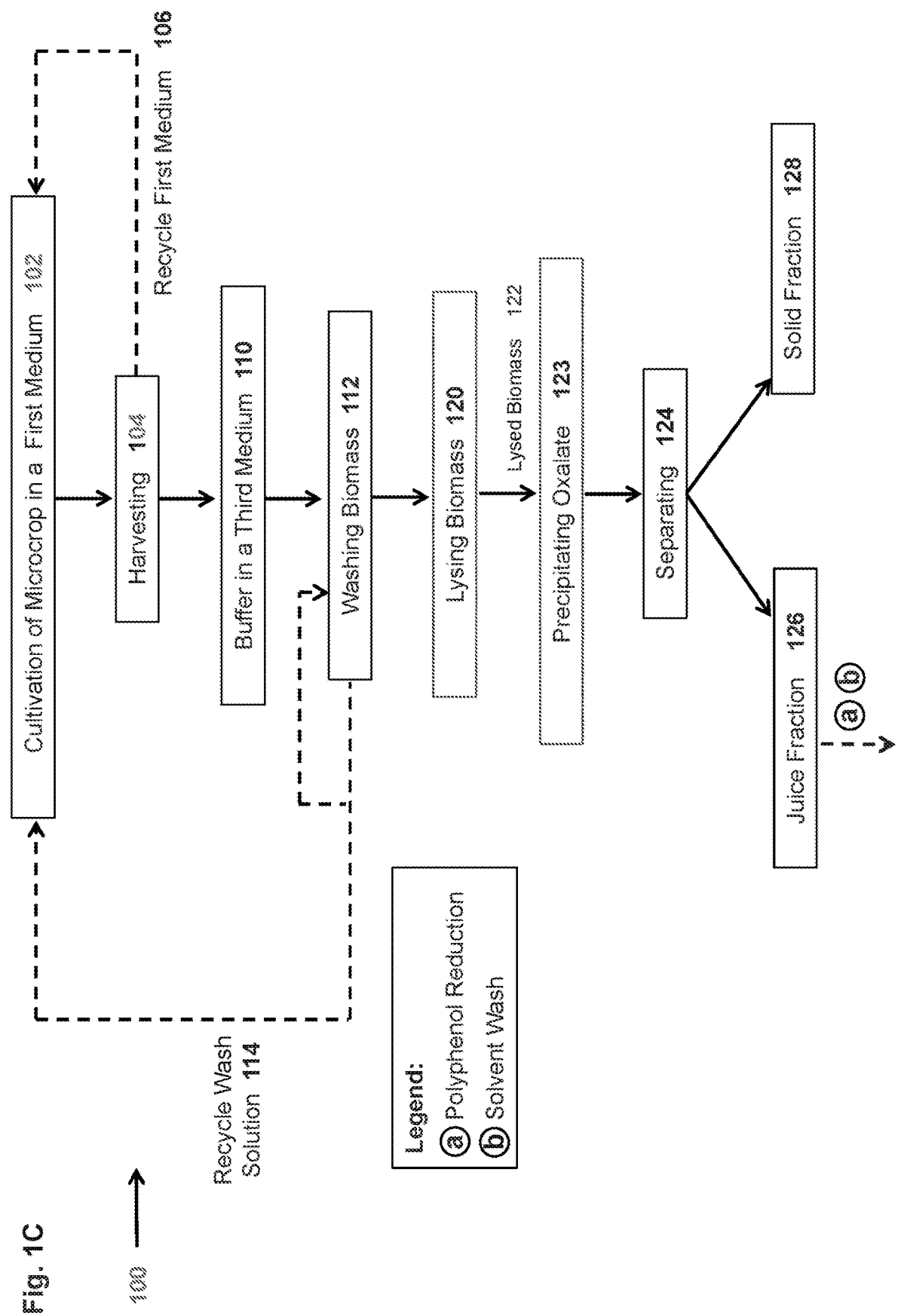
FIG. 1C is a flow diagram illustrating a system for cultivating, harvesting, and processing a microcrop for the production of a protein concentrate having a reduced oxalic acid content according to a specific example embodiment of the disclosure.
Figure 1D:
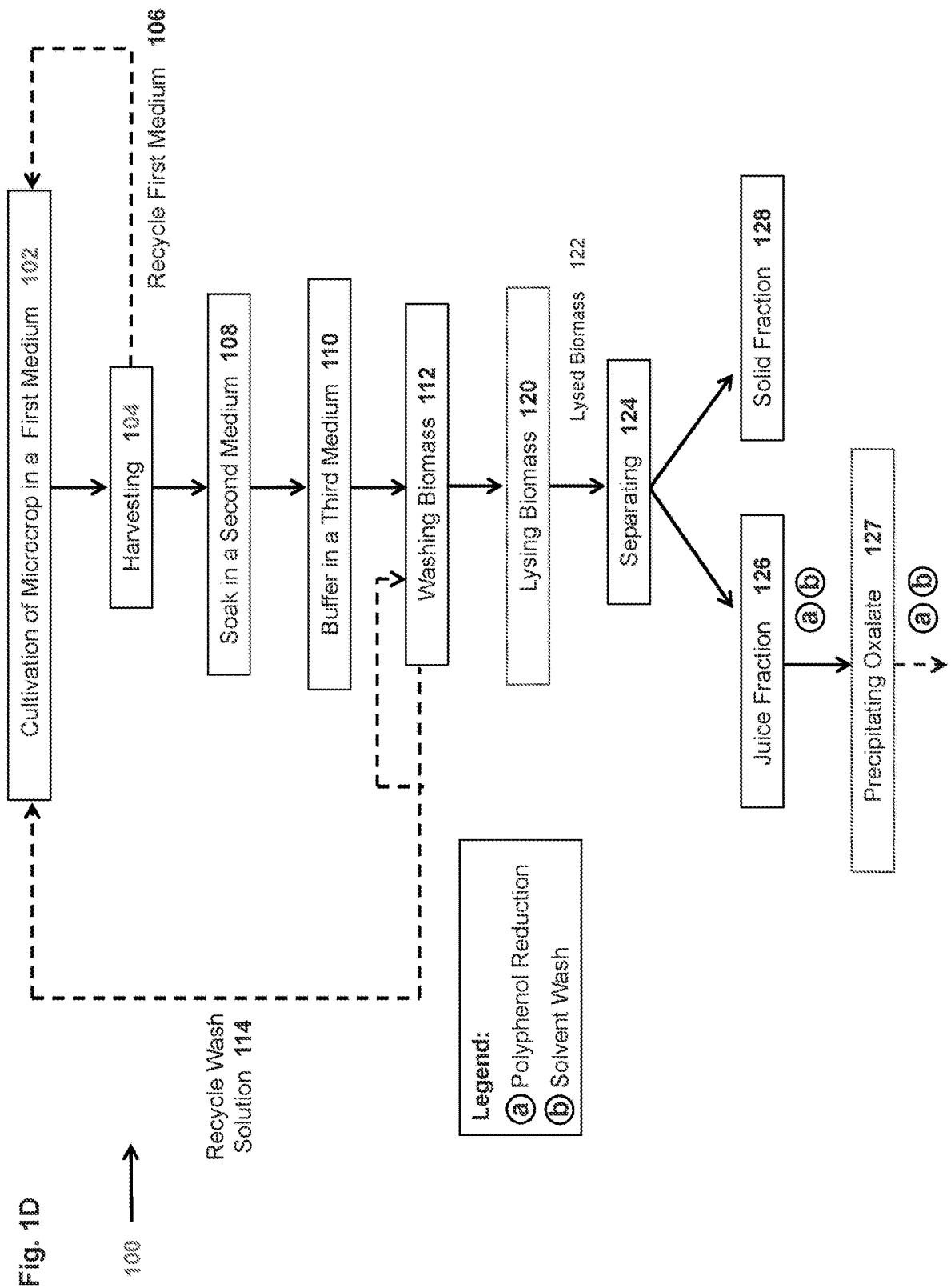
FIG. 1D is a flow diagram illustrating a system for cultivating, harvesting, and processing a microcrop for the production of a protein concentrate having a reduced oxalic acid content according to a specific example embodiment of the disclosure.

As illustrated in FIG. 1B and FIG. 1D, in some embodiments a harvested biomass may be soaked 108 in a second medium (e.g., water, distilled water, reverse osmosis or nanofiltered water, a nutrient composition, and/or recycled fluid 260, 254). According to some embodiments, a second medium may be configured to have a low calcium composition (e.g., having a calcium concentration of ≤about 5 ppm). In some embodiments, a second medium may be configured to have (1) a low nitrogen composition (e.g., having a nitrogen concentration of ≤about 1 ppm) or (2) a low calcium composition (e.g., having a calcium concentration of ≤about 5 ppm) or (3) a low nitrogen composition (e.g., having a nitrogen concentration of ≤about 1 ppm) and a low calcium composition (e.g., having a calcium concentration of ≤about 5 ppm). In some embodiments soaking a biomass may comprise submerging a biomass in a second medium to form a biomass slurry, with soaking extending for an extended period of time (e.g., 24 hours) with or without agitation.

According to some embodiments, as illustrated in FIG. 1B and FIG. 1C, a biomass may be buffered in a third medium (e.g., 110). A third medium may comprise water, distilled water, reverse osmosis, nanofiltered water, and/or any desired portion of recycled fluid (e.g., a reject stream from filtration 260, 254), according to some embodiments. In some embodiments buffering a biomass may comprise submerging a biomass in a third medium for an extended period of time (e.g., 24 hours) with or without agitation.

In some embodiments, and as illustrated in FIGS. 1A, 1B, 1C, and 1D, processing a biomass may comprise a wash procedure 112. A wash procedure 112 may be performed on a biomass: (1) after harvesting (FIG. 1A); or (2) after harvesting and soaking (FIG. 1B); or (3) after harvesting and buffering (FIG. 1C); or (4) or after harvesting, soaking, and buffering (FIG. 1D). Washing a biomass may increase protein purity and/or yield. In some embodiments a wash procedure may be performed by exposing (e.g., submerging, spraying) at least one surface of a biomass to a wash solution (e.g., water, growth medium, antimicrobial solution). A wash solution, in some embodiments, may be combined with a biomass (e.g., first portion, second portion) to form a slurry. In some embodiments, a biomass may be washed with a first wash solution, a second wash solution, a third wash solution, or any combination thereof. Some or all of a wash solution (e.g., first wash solution, second wash solution, and/or third wash solution) may be separated from a biomass, collected, and reused/recycled 114. In some embodiments a recycled wash solution may be used as growth medium (e.g., first medium) in the bioreactor system 102, according to some embodiments.

As illustrated in FIGS. 1A, 1B, 1C, and 1D, according to some embodiments a biomass may be lysed 120 to form a lysed biomass 122. Lysing 120 may be performed on a biomass: (1) after harvesting 104; or (2) after harvesting and soaking 108; or (3) after harvesting and buffering 110; or (4) or after harvesting, soaking, and buffering; or (5) after harvesting and washing 112 (FIG. 1A); or (6) after harvesting, soaking, and washing (FIG. 1B); or (7) after harvesting, buffering, and washing (FIG. 1C); or (8) after harvesting, soaking, buffering, and washing (FIG. 1D). According to some embodiments, lysing 120 may be achieved using a combination of mechanical, chemical, and/or ultrasonic (e.g., sonication) methods. Lysing 120 may include, for example, chopping, shredding, smashing, pressing, tearing, ultrasonic treatment (e.g., sonication), lysis by osmotic pressure, chemical treatments that degrade biological structures, or any combination thereof. In some embodiments, lysing 120 is achieved in a mechanical way (also referred to as milling), for example, by milling, grinding, or shredding the biomass to generate a lysed biomass. A lysing process 120 may be achieved using, for example, a shear mill, a ball mill, a colloid mill, a knife mill, a hammer mill, a grinding mill, a puree machine, a filter press, a mechanical press or any combination thereof. In some embodiments, lysing may be performed at temperatures below room temperature (e.g., 12° C.).

As illustrated in FIGS. 1A, 1B, and 1C, and 1D, a biomass (e.g., Lemna) may be separated 124 to generate a juice fraction 126 and a solid fraction 128. A juice fraction (e.g., first portion, second portion) may include a protein-rich liquid and/or at least about some solid particles (e.g., carbohydrates, fiber). Separating a biomass to form a juice fraction and a solid fraction may involve pressing (e.g., belt press, filter press), centrifugation, filtration, pressurized filtration, or any combination thereof. Interchangeable unit operations for separating a biomass include, for example, a decanter centrifuge, a belt press, a fan press, a rotary press, a screw press, a filter press, a finisher press, or any combination thereof.

Separating a biomass may be performed at any desired temperature. In some embodiments, separating may be performed at temperatures below room temperature (e.g., 12° C.), for example, to decrease proteolytic activity.

According to some embodiments, and as illustrated in FIGS. 1A, 1B, and 1C, at least some soluble oxalic acid may be removed from a lysed biomass by conversion to calcium oxalate and precipitation 123. In some embodiments, precipitating oxalate from a lysed biomass may include mixing at least a portion of a lysed biomass with at least one calcium salt (e.g., calcium chloride, calcium acetate). Precipitating oxalate from a lysed biomass, in some embodiments, may include mixing at least a portion of the lysed biomass with a calcium carbonate or calcium hydroxide solution. Precipitated oxalate may be removed from the biomass by centrifugation and/or filtration, according to some embodiments.

According to some embodiments, as illustrated in FIG. 1D, at least some soluble oxalic acid may be removed from a juice fraction by conversion to calcium oxalate and precipitation 127. In some embodiments, precipitating a juice fraction may include mixing at least a portion of the juice fraction with at least one calcium salt (e.g., calcium chloride, calcium acetate). Precipitating a juice fraction, in some embodiments, may include mixing at least a portion of the juice fraction with a calcium carbonate or calcium hydroxide solution.

In some embodiments, a juice fraction 126, may undergo a processing step for the reduction of at least one polyphenol (a). A polyphenol reduction process may comprise passing a juice fraction 126, through a single or a series (e.g., at least two, at least three) of ion exchange resins. A polyphenol reduction process may be performed, in some embodiments, either before or after precipitating a juice fraction 127. In some embodiments, a polyphenol reduction process may reduce a polyphenol (e.g., a tannin) content of a juice fraction 126 by at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%.

According to some embodiments, a juice fraction 126 may undergo a solvent wash (b). A solvent wash may be performed, in some embodiments, either before or after precipitating a juice fraction 127. A solvent wash of a juice fraction 126, may comprise at least one solvent (e.g., ethanol, methanol), in some embodiments. According to some embodiments, a solvent wash of a juice fraction 126, may result in a reduced fat content (e.g., about 2% of a dry protein concentrate or less by weight) and/or a reduced chlorophyll content (e.g., visually perceivable reduction in green coloration) compared to unwashed counterparts.

FIGS. 2A, 2B, and 2C

FIGS. 2A, 2B, and 2C are schematic diagrams illustrating a process 200 for producing a protein concentrate having a reduced oxalic acid content from a microcrop (e.g., aquatic plant species, Lemna, algal species) according to specific example embodiments of the disclosure.

As illustrated in FIGS. 2A, 2B, and 2C, according to some embodiments a biomass may be lysed 220 to form a lysed biomass 222. Lysing 220 may be performed on a biomass: (1) after harvesting 104; or (2) after harvesting and soaking 108; or (3) after harvesting and buffering 110; or (4) or after harvesting, soaking, and buffering; or (5) after harvesting and washing 112 (FIG. 1A); or (6) after harvesting, soaking, and washing (FIG. 1B); or (7) after harvesting, buffering, and washing (FIG. 1C); or (8) after harvesting, soaking, buffering, and washing (FIG. 1D). Lysing 120 may include, for example, chopping, shredding, smashing, pressing, tearing, ultrasonic treatment (e.g., sonication), lysis by osmotic pressure, chemical treatments that degrade biological structures, or any combination thereof. A lysing process 120 may be achieved using, for example, a shear mill, a ball mill, a colloid mill, a knife mill, a hammer mill, a grinding mill, a puree machine, a filter press, a mechanical press or any combination thereof. In some embodiments, lysing may be performed at temperatures below room temperature (e.g., 12° C.).

According to some embodiments, and as illustrated in FIG. 2B, at least some soluble oxalic acid may be removed from a lysed biomass by conversion to oxalate and precipitation 223. In some embodiments, precipitating oxalate from a lysed biomass may include mixing at least a portion of a lysed biomass with at least one calcium salt (e.g., calcium chloride, calcium acetate). Precipitating oxalate from a lysed biomass, in some embodiments, may include mixing at least a portion of the lysed biomass with a calcium carbonate or calcium hydroxide solution. Precipitated oxalate may be removed from the biomass by centrifugation and/or filtration, according to some embodiments.

As illustrated in FIGS. 2A, 2B, and 2C, a biomass (e.g., *Lemna*) may be separated 224 to generate a juice fraction 226 and a solid fraction 228. A juice fraction (e.g., first portion, second portion) may include a protein-rich liquid and/or at least about some solid particles (e.g., carbohydrates, fiber). Separating a biomass to form a juice fraction and a solid fraction may involve pressing (e.g., belt press, filter press), centrifugation, filtration, pressurized filtration, or any combination thereof. Interchangeable unit operations for separating a biomass include, for example, a decanter centrifuge, a belt press, a fan press, a rotary press, a screw press, a filter press, a finisher press, or any combination thereof.

Separating a biomass may be performed at any desired temperature. In some embodiments, separating may be performed at temperatures below room temperature (e.g., 12° C.), for example, to decrease proteolytic activity and/or microbial growth.

According to some embodiments, as illustrated in FIG. 2C, at least some soluble oxalic acid may be removed from a juice fraction by conversion to calcium oxalate and precipitation 227. In some embodiments, precipitating a juice fraction may include mixing at least a portion of the juice fraction with at least one calcium salt (e.g., calcium chloride, calcium acetate). Precipitating a juice fraction, in some embodiments, may include mixing at least a portion of the juice fraction with a calcium carbonate or calcium hydroxide solution. Precipitated calcium oxalate may be removed from the biomass by centrifugation and/or filtration, according to some embodiments.

As illustrated in FIGS. 2A, 2B, and 2C, a juice fraction 226 may be separated 236 to generate a first juice 238 and a first cake 240, according to some embodiments. A first juice may include a dissolved protein. Separating a juice fraction, in some embodiments, may include centrifugation, filtration, pressurized filtration, or any combination thereof. Two or more unit operations (e.g., interchangeable unit operations) may be used to separate a juice fraction including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof. Microfiltration may be used, in some embodiments, to separate 236 a juice fraction 226 into a first juice 238 and a first cake 240. In some embodiments, separating 236 may be performed at temperatures below room temperature (e.g., 12° C.).

In some embodiments, a solid fraction 228 may be further separated 230 to form a second juice 232 and a first solid 234. A second juice 232 may include a protein-rich liquid and/or at least some solid particles (e.g., carbohydrates, fiber). Separating 230 a solid fraction 228 to form a second juice 232 and a first solid 234 may involve pressing (e.g., screw press), centrifugation, filtration, pressurized filtration, or any combination thereof. Interchangeable unit operations for separating 230 a solid fraction include, for example, a decanter centrifuge, a belt press, a fan press, a rotary press, a screw press, a filter press, a finisher press, or any combination thereof.

As shown in FIGS. 2A, 2B, and 2C, according to some embodiments, a process for growing, harvesting, and separating a microcrop (e.g., aquatic plant species, *Lemna*, algal species) may be single cycle and at least one of a first cake (e.g., 240) and a second cake (e.g., 246) which are collected at other stages in the cycle (e.g., separation of a juice fraction yields a first cake) may be combined with a first solid to form a solid mixture, and the solid mixture may be further processed.

In some embodiments a process for growing, harvesting, and separating a microcrop (e.g., aquatic plant species, *Lemna*, algal species) may be multiple cycles or a continuous process such that one or more of a first cake and a second cake that are collected in an earlier cycle may be combined with a solid fraction from a subsequent cycle prior to separation of the solid fraction.

As illustrated in FIGS. 2A, 2B, and 2C, in some embodiments, a first cake 240 and a second juice 232 may be combined and further separated 242 to form a third juice 244 and a second cake 246. Separating 242 a first cake 240, a second juice 232, or any combination thereof may involve vibratory separation, centrifugation, filtration, pressurized filtration, or any combination thereof. Several different interchangeable unit operations may be used to separate including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof.

As illustrated in FIGS. 2A, 2B, and 2C, a first juice 238, a third juice 244, or any combination thereof may be filtered 246 one or more times to generate a first soluble protein 250 and a first reject stream 248. A first filtration may involve microfiltration. Suitable filter sizes for microfiltration may include, in some embodiments, ≤about 10 µm, or ≤about 5 µm, or ≤about 3 µm, or ≤about 2 µm, or ≤about 1 µm, or ≤about 0.5 µm, or ≤about 0.4 µm, or ≤about 0.3 µm, or ≤about 0.2 µm, or ≤about 0.1 µm. A first soluble protein product may be chilled and/or stored at a temperature below room temperature (e.g., 12° C.).

According to some embodiments, a first soluble protein 246 may be subjected to a second filtration 252 to form a second soluble protein 256 and a second reject stream 254. A second filtration may include ultrafiltration, nanofiltration, and/or reverse osmosis filtration. In some embodiments, a second protein product may be chilled and/or stored at a temperature below room temperature (e.g., 12° C.).

In some embodiments a process may be used to reduce a moisture content of a first soluble protein 250, a second soluble protein 256, or any combination thereof (collectively "a soluble protein product"). An evaporation process may be used to reduce a moisture content of a soluble protein product, according to some embodiments. As shown in FIGS. 2A, 2B, and 2C, a moisture content of a soluble protein product (e.g., a second soluble protein) may be reduced, in some embodiments, by nanofiltration or reverse osmosis filtration 258 to form a concentrated protein product with reduced oxalic acid 262. A permeate of nanofiltration or reverse osmosis filtration process 258 may be recycled (e.g., dilution fluid for lysis 260; wash solution), according to some embodiments.

A soluble protein product (e.g., a first soluble protein 250, a second soluble protein 256, concentrated protein product with reduced oxalic acid 262) may be dried 264 to generate a dry protein concentrate, according to some embodiments. A drying procedure may be performed using a mechanism including, for example, a spray dryer, double drum dryer, flash dryer, an evaporator, or any combination thereof.

In some embodiments, a juice fraction 226, a first juice 241, a second juice 232, a third juice 246, and/or a soluble protein 251 may undergo a processing step for the reduction of at least one polyphenol (a). A polyphenol reduction process may comprise passing a juice fraction 226, a first juice 241, a second juice 232, a third juice 246, and/or a soluble protein 251 through a series (e.g., at least two, at least three) of ion exchange resins. In some embodiments, a polyphenol reduction process may reduce a polyphenol (e.g., a tannin) content of a juice fraction 226, a first juice 241, a second juice 232, a third juice 246, and/or a soluble protein 251 by at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%.

In some embodiments, a soluble protein 251 may undergo a solvent wash (b). Solvent washing (b) may also follow drying 255. A solvent wash of a soluble protein product 251 and/or a solvent wash following drying 255, may comprise at least one solvent (e.g., ethanol, methanol), in some embodiments. According to some embodiments, a solvent wash of a soluble protein product 251 and/or a solvent wash following drying 255, may result in a reduced fat content (e.g., about 2% of a dry protein concentrate or less by weight) and/or a reduced chlorophyll content (e.g., visually perceivable reduction in green coloration) compared to unwashed counterparts.

In some embodiments, a first solid 234 and/or solid mixture may be further processed to generate one or more carbohydrate-rich products.

Systems of Extracting Proteins and/or Carbohydrate-Rich Products from Aquatic Species Embodiments of the disclosure also provide systems of extracting proteins and carbohydrate rich products from aquatic species. Such systems may include, for example: a lysing unit (e.g., 120/220) for lysing a biomass to generate a lysed biomass; a first separating unit (e.g., 224) for separating the lysed biomass to generate a juice fraction and a solid fraction; a second separating unit (e.g., 236) for forming a first juice and a first cake; a third separating unit (e.g., 230) for forming a first solid and a second juice; a fourth separating unit (e.g., 242) for forming a second cake and a third juice; a first filtration unit (e.g., 246) for forming: a first soluble protein and a first reject stream; a second filtration unit (e.g., 252) for forming a second soluble protein and second reject stream; a dewatering unit (e.g., 258) for forming a concentrated protein and a permeate; and a protein drying unit (e.g., 264) for drying a soluble protein product to generate a dry protein concentrate. Summarized in Table 4 are apparatuses that can be included in the units described above.

TABLE 4

| | Example Apparatuses |
|---|---|
| Lysing Unit (e.g., 220) | Shear Mill, Ball Mill, Colloid Mill, Knife Mill, Hammer Mill, Grinding Mill, Puree Machine, Filter Press |
| First Separating Unit (e.g., 224) | Decanter Centrifuge, Belt Press, Fan Press, Rotary Press, Screw Press, Filter Press, Finisher Press |
| Second Separating Unit (e.g., 236) | High-speed Disc Stack Centrifuge, Circular Vibratory Separator, Linear/inclined Motion Shaker, Decanter Centrifuge, Filter Press, Pressurized Filtration Mechanisms, Microfiltration Module, Vacuum Filtration Apparatus |
| Third Separating Unit (e.g., 230) | Belt Press, Fan Press, Rotary Press, Screw Press, Filter Press, Finisher Press, Decanter Centrifuge |
| Fourth Separating Unit (e.g., 242) | High-speed Disc Stack Centrifuge, Circular Vibratory Separator, Linear/inclined Motion Shaker, Decanter Centrifuge, Filter Press, Pressurized Filtration Mechanisms, Microfiltration, Vacuum Filtration Apparatus |
| First Filtration Unit (e.g., 246) | Microfiltration Module *Any of the above modules may be configured as single or multistage crossflow membrane filtration systems. |
| Second Filtration Unit (e.g., 252) | Ultrafiltration Module, Nanofiltration Module, Reverse Osmosis Filtration Module *Any of the above modules may be configured as single or multistage crossflow membrane filtration systems. |
| Dewatering Unit (e.g., 258) | Rising Film Evaporator, Falling Film Evaporator, Natural Circulation Evaporator (vertical or horizontal), Agitated-Film Evaporator, Multiple-effect Evaporator, Vacuum Evaporation Apparatus, Nano-filtration Module, Reverse Osmosis Filtration Module |
| Protein Drying Unit | Spray dryer, Drum dryer, Flash dryer |

It is understood that the listed apparatuses for each unit are for illustration purposes only, and this is not intended to limit the scope of the application. A specific combination of these or other apparatuses or units can be configured in such a system for the intended use based on the teachings in the application.

Persons skilled in the art may make various changes in the shape, size, number, separation characteristic, and/or arrangement of parts without departing from the scope of the instant disclosure. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. Where desired, some embodiments of the disclosure may be practiced to the exclusion of other embodiments.

Also, where ranges have been provided, the disclosed endpoints may be treated as exact and/or approximations (e.g., read without or with "about") as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In some embodiments, variation may simply be +/−10% of the specified value. In addition, it may be desirable, in some embodiments, to mix and match range endpoints. Also, in some embodiments, each figure disclosed (e.g., in one or more of the examples, tables, and/or drawings) may form the basis of a range (e.g., depicted value+/−about 10%, depicted value+/−about 50%, depicted value+/−about 100%) and/or a range endpoint. With respect to the former, a value of 50 depicted in an example, table, and/or drawing may form the basis of a range of, for example, about 45 to about 55, about 25 to about 100, and/or about 0 to about 100.

These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

What is claimed is:

1. A method of treating a biomass comprising an aquatic plant species to generate a product comprising a soluble protein, the method comprising:
    lysing the biomass to form a lysed biomass;
    precipitating oxalate from the lysed biomass,
    separating the lysed biomass to generate a juice fraction and a solid fraction,
    separating the juice fraction to generate a first juice and a first cake; and
    filtering the first juice to generate a first soluble protein and a first reject stream, wherein the first soluble protein comprises an oxalic acid content of less than about 0.6% DMB.

2. The method of claim 1, wherein the first soluble protein comprises an oxalic acid content of less than about 0.1% DMB.

3. The method of claim 1, wherein in the first soluble protein comprises an oxalic acid content of less than about 0.05% DMB.

4. The method of claim 1 further comprising soaking the biomass in a first medium to form a soaked biomass, wherein the first medium comprises: less than about 8 ppm of a calcium source, or less than about 4 ppm of a nitrogen source, or both.

5. The method of claim 4 further comprising buffering the soaked biomass in a second medium.

6. The method of claim 1 further comprising precipitating oxalate from the juice fraction.

7. The method of claim 1 further comprising filtering the first soluble protein to generate a second soluble protein and a second reject stream.

8. The method of claim 7 further comprising filtering the second soluble protein to generate a concentrated protein product and a permeate.

9. The method of claim 8 further comprising drying the concentrated protein product to generate a dry protein concentrate, wherein the dry protein concentrate has a protein concentrate of at least about 50% by weight.

10. The method of claim 8 further comprising drying the concentrated protein product to generate a dry protein concentrate, wherein the dry protein concentrate has a solubility value of at least 50%.

11. The method of claim 8 further comprising drying the concentrated protein product to generate a dry protein concentrate, wherein the dry protein concentrate has a dispersibility value of at least 50%.

12. The method of claim 1, wherein the aquatic plant species is *Lemna*.

13. A method of treating a biomass comprising an aquatic plant species to generate a product comprising a soluble protein, the method comprising:
    lysing the biomass to form a lysed biomass;
    separating the lysed biomass to generate a juice fraction and a solid fraction,
    precipitating oxalate from the juice fraction,
    separating the juice fraction to generate a first juice and a first cake; and
    filtering the first juice to generate a first soluble protein and a first reject stream,
        wherein the first soluble protein comprises an oxalic acid content of less than about 0.6% DMB.

14. The method of claim 13, wherein the first soluble protein comprises an oxalic acid content of less than about 0.1% DMB.

15. The method of claim 13, wherein in the first soluble protein comprises an oxalic acid content of less than about 0.05% DMB.

16. The method of claim 13 further comprising soaking the biomass in a first medium to form a soaked biomass, wherein the first medium comprises: less than about 8 ppm of a calcium source, or less than about 4 ppm of a nitrogen source, or both.

17. The method of claim 16 further comprising buffering the soaked biomass in a second medium.

18. The method of claim 13 further comprising precipitating oxalate from the lysed biomass.

19. The method of claim 13 further comprising filtering the first soluble protein to generate a second soluble protein and a second reject stream.

20. The method of claim 19 further comprising filtering the second soluble protein to generate a concentrated protein product and a permeate.

21. The method of claim 20 further comprising drying the concentrated protein product to generate a dry protein concentrate, wherein the dry protein concentrate has a protein concentration of at least about 50% by weight.

22. The method of claim 20 comprising drying the concentrated protein product to generate a dry protein concentrate, wherein the dry protein concentrate has a solubility value of at least 50%.

23. The method of claim 20 further comprising drying the concentrated protein product to generate a dry protein concentrate, wherein the dry protein concentrate has a dispersibility value of at least 50%.

24. The method of claim 13, wherein the aquatic plant species is *Lemna*.

25. A method of cultivating and treating a biomass comprising an aquatic plant species to generate a product comprising a soluble protein, the method comprising:
    cultivating the aquatic plant species in a first medium to form a biomass, wherein the first medium comprises at least one of (i) calcium concentration of at least 20 ppm and (ii) one or more anti-photosynthetic dyes;

harvesting the biomass;

lysing the biomass to form a lysed biomass;

precipitating oxalate from the lysed biomass;

separating the lysed biomass to generate a juice fraction and a solid fraction, separating the juice fraction to generate a first juice and a first cake; and filtering the first juice to generate a first soluble protein and a first reject stream, wherein the soluble protein comprises an oxalic acid content of less than 0.6% DMB.

26. The method of claim 25, wherein the one or more anti-photosynthetic dyes is selected from a disodium salt of (n-ethyl-n-[4-[[4-[ethyl[(3 sulfophenyl)methyl]aminol-phenyl](2-sulfophenyl)-methylene)]2,5-cyclohexadien-1-ylidene]-3-sulfobenzenemethanaminium hydroxide inner salt, a trisodium salt of (4E)-5-oxo-1-(4-sulfonatophenyl)-4-[(4-sulfonatophenyl)hydrazonoJ-3-pyrazolecarboxylate, diazanium; 2-[[4-fethyl-[(3-sulfonatophenyl)methyl]aminolphenyl]-[4-fethyl-[(3-sulfonatophenyl) methyl] azaniumylidene] cyclohexa-2,5-dien-1-ylidene]methyl]benzenesulfonate, benzyl-[4-[[4-[benzyl(ethyl)amino]phenyl]-(5-hydroxy-2,4-disulfophenyl)methylidene]cyclohexa-2,5-dien-1-ylidene]-ethylazanium, a disodium salt of 2-(1,3-dioxoinden-2-yl)quinoline-6,8-disulfonate, or combinations thereof.

27. The method of claim 25, further comprising soaking the biomass in a second medium, wherein the second medium comprises: less than about 8 ppm of a calcium source, or less than about 4 ppm of a nitrogen source, or both.

28. The method of claim 25, wherein the first soluble protein comprises an oxalic acid content of less than 0.1% DMB.

29. The method of claim 25, wherein the first soluble protein comprises an oxalic acid content of less than 0.05% DMB.

30. The method of claim 27, further comprising buffering the biomass in a third medium.

31. The method of claim 25, further comprising filtering the first soluble protein to generate a second soluble protein and a second reject stream.

32. The method of claim 31 further comprising filtering the second soluble protein to generate a concentrated protein product and a permeate.

33. The method of claim 32 further comprising drying the concentrated protein product to generate a dry protein concentrate, wherein the dry protein concentrate has a protein concentration of at least about 50% by weight.

34. The method of claim 32 further comprising drying the concentrated protein product to generate a dry protein concentrate, wherein the dry protein concentrate has a solubility value of at least 50%.

35. The method of claim 32 further comprising drying the concentrated protein product to generate a dry protein concentrate, wherein the dry protein concentrate has a dispersibility value of at least 50%.

36. The method of claim 25, wherein the aquatic plant species is *Lemna*.

* * * * *